United States Patent [19]
Adam et al.

[11] Patent Number: 6,071,925
[45] Date of Patent: Jun. 6, 2000

[54] 1,3,8-TRIAZASPIRO[4,5]DECAN-4-ONE DERIVATIVES

[75] Inventors: Geo Adam, Schopfheim, Germany; Andrea Cesura, Basel, Switzerland; Guido Galley, Rheinfelden, Germany; François Jenck, Riedisheim, France; Frederick Monsma, Jr., Madison, N.J.; Stephan Röver, Inzlingen; Jürgen Wichmann, Steinen, both of Germany

[73] Assignee: Hoffmann-La Roche Inc., Nutley, N.J.

[21] Appl. No.: 09/009,457

[22] Filed: Jan. 20, 1998

[30] Foreign Application Priority Data

Jan. 30, 1997 [EP] European Pat. Off. ............ 97101409
Nov. 5, 1997 [EP] European Pat. Off. ............ 97119311

[51] Int. Cl.[7] ...................... A61K 31/445; C07D 211/98
[52] U.S. Cl. ............................. 514/278; 546/20
[58] Field of Search ................ 546/20; 514/278

[56] References Cited

U.S. PATENT DOCUMENTS

| | | | |
|---|---|---|---|
| 4,076,821 | 2/1978 | Tsuda et al. | 424/263 |
| 4,160,836 | 7/1979 | Vandenberx et al. | 546/20 |
| 4,329,353 | 5/1982 | Stokbroekx et al. | 424/267 |
| 4,707,484 | 11/1987 | Berger et al. | 514/278 |
| 4,880,802 | 11/1989 | Schohe et al. | 514/222.2 |
| 5,026,857 | 6/1991 | Schohe et al. | 514/319 |
| 5,039,804 | 8/1991 | Feldman et al. | 546/70 |
| 5,153,225 | 10/1992 | Schohe et al. | 514/602 |
| 5,298,513 | 3/1994 | Schohe et al. | 514/319 |
| 5,463,105 | 10/1995 | Schohe et al. | 560/29 |

FOREIGN PATENT DOCUMENTS

| | | |
|---|---|---|
| 091 510 | 10/1983 | European Pat. Off. . |
| 0 270 947 A2 | 11/1987 | European Pat. Off. . |
| 273 168 | 11/1987 | European Pat. Off. . |
| 539 803 | 10/1992 | European Pat. Off. . |
| 44 05 178 | 8/1995 | Germany . |
| 12171 | 1/1977 | Japan . |
| 139384 | of 1984 | Japan . |
| 153662 | of 1989 | Japan . |
| 1099845 | 6/1984 | U.S.S.R. . |
| WO 95/22544 | 8/1995 | WIPO . |

OTHER PUBLICATIONS

Derwent Abstract, DE 4405178.
Derwent Abstract, EP 539 803.
Bunzow, James R., et al., *FEBS Letters*, 347:284–288 (1994).
Cheng, Yung–Chi and William H. Prusoff, *Biochem. Pharmacol*, 22:3099–3108 (1973).
Julius, David, *Nature*, 377:476 (1995).
Mattson, Ronald J., et al., *J. Org. Chem.*, 55:2552–2554 (1990).
Mavunkel, Babu J., et al., *J. Med. Chem.*, 39:3169–3173 (1996).
Tschaen, David M., et al., *J. Org. Chem.*, 60:4324–4330 (1995).

Primary Examiner—Mukund J. Shah
Assistant Examiner—Pavanaram K Sripada
Attorney, Agent, or Firm—George W. Johnston; Patricia S. Rocha-Tramaloni; Eileen M. Ebel

[57] ABSTRACT

The present invention relates to compounds of the formula

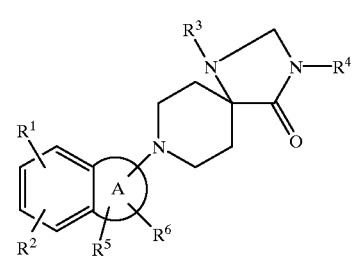

I wherein
$R^1$ and $R^2$ are each independently hydrogen, lower alkyl, lower alkoxy or halogen;
$R^3$ is phenyl, which is unsubstituted or substituted by lower alkyl, $CF_3$, lower alkoxy or halogen;
$R^4$ is hydrogen, lower alkyl, lower alkenyl, —C(O)-lower alkyl, —C(O)-phenyl, lower alkyl-C(O)-phenyl, lower alkylene-C(O)O-lower alkyl, lower alkantriyl-di-C(O)O-lower alkyl, hydroxy-lower alkyl, lower alkyl-O-lower alkyl, lower alkyl-CH(OH)$CF_3$, phenyl or benzyl,
$R^5$ and $R^6$ are each independently hydrogen, phenyl, lower alkyl or di-lower alkyl or $R^5$ and $R^6$ together with the carbon atoms to which they are bound form a phenyl ring, or
$R^5$ and one of $R^1$ or $R^2$ together with the carbon atoms to which they are bound form a saturated or unsaturated 6 membered ring,
A is a 4–7 membered saturated ring, their racemates and the enantiomers thereof, and the
pharmaceutically acceptable acid addition salts thereof which are agonists and/or antagonists of the OFQ receptor.

167 Claims, No Drawings

1,3,8-TRIAZASPIRO[4,5]DECAN-4-ONE DERIVATIVES

The present invention relates to compounds of the formula

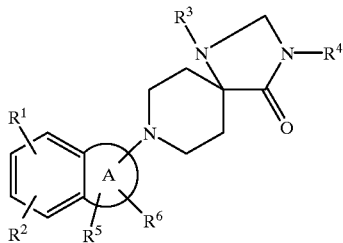

wherein
$R^1$ and $R^2$ are each independently hydrogen, lower alkyl, lower alkoxy or halogen;
$R^3$ is phenyl which is unsubstituted or substituted by lower alkyl, $CF_3$, lower alkoxy or halogen;
$R^4$ is hydrogen, lower alkyl, lower alkenyl. —C(O)-lower alkyl, —C(O)-phenyl, lower alkyl-C(O)-phenyl, lower alkylene-C(O)O-lower alkyl, lower alkantriyl-di-C(O)O-lower alkyl, hydroxy-lower alkyl, lower alkyl-O-lower alkyl, lower alkyl-CH(OH)CF$_3$, phenyl or benzyl,
$R^5$ and $R^6$ are each independently hydrogen, phenyl, lower alkyl or di-lower alkyl or $R^5$ and $R^6$ together with the carbon atoms to which they are bound form a phenyl ring, and
$R^5$ and one of $R^1$ or $R^2$ together with the carbon atoms to which they are bound form a saturated or unsaturated 6 membered ring,
A is a 4–7 membered saturated ring which optionally contains a heteroatom selected from O or S, their racemates and the enantiomers thereof and the pharmaceutically acceptable acid addition salts thereof.

The compounds of formula I and their salts are distinguished by valuable therapeutic properties. It has surprisingly been found that the compounds of the present invention are agonists and/or antagonists of the OFQ receptor. Consequently they will be useful in the treatment of psychiatric, neurological and physiological disorders, especially, but not limited to, amelioration of symptoms of anxiety and stress disorders, depression, trauma, memory loss due to Alzheimer's disease or other dementias, epilepsy and convulsions, acute and/or chronic pain conditions, symptoms of withdrawal from drugs of addiction, control of water balance, Na$^+$ excretion, arterial blood pressure disorders and eating disorders such as obesity.

Orphanin FQ (OFQ), a seventeen amino-acid-long peptide (F-G-G-F-T-G-A-R-K-S-A-R-K-L-A-N-Q), has been isolated from rat brain and is a natural ligand for a G-protein coupled receptor (OFQ-R), found at high levels in brain tissue.

OFQ exhibits agonistic action at the OFQ-R both in vitro and in vivo.

Julius (Nature 377,476, [1995]) discusses the discovery of OFQ noting that this peptide shares greatest sequence similarity with dynorphin A, an established endogenous ligand for opioid receptors. OFQ inhibits adenylate cyclase in CHO(LC 132$^+$) cells in culture and induces hyperalgesia when administered intra-cerebroventricularly to mice. The pattern of results indicate that this heptadecapeptide is an endogenous agonist of the LC 132 receptor and it appears to have pro-nociceptive properties. It was described that when injected intra-cerebroventricularly in mice, OFQ slowed down locomotive activity and induced hyperalgesia. It was concluded that OFQ may act as a brain neurotransmitter to modulate nociceptive and locomotive behavior.

Objects of the present invention are the (compounds of formula I and pharmaceutically acceptable addition salts thereof, racemic mixtures and their corresponding enantiomers, the preparation of the above-mentioned compounds, medicaments or pharmaceutical compositions containing them and their processes for making as well as the use of the above-mentioned compounds in the control or prevention of illnesses, especially of illnesses and disorders of the kind referred to earlier, or in the manufacture of corresponding medicaments.

The following definitions of terms used in the present description apply respective of whether the terms in question appear alone or in combination.

As used herein, the term "lower alkyl" denotes a straight- or branched-chain alkyl group containing from 1 to 6 carbon atoms, for example, methyl, ethyl, propyl, isopropyl, n-butyl, i-butyl, 2-butyl, t-butyl.

The term "halogen" denotes chlorine, iodine, fluorine and bromine.

The term "lower alkoxy" denotes a group wherein the alkyl residues is as defined above, and which is attached via an oxygen atom.

The term "4–7 membered saturated ring which optionally contains a heteroatom selected from O or S" for A denotes a cyclobutyl, cyclopentyl, cyclohexyl, or cycloheptyl ring where one of the carbon atoms can be replaced by a heteroatom selected from O or S. For example, A together with the ring to which it is bound may represent, when no heteroatom is present, bicyclo[4.2.0]octa-1,3,5-triene; indan (2,3-dihydroindene); 1,2,3,4-tetrahydronaphthalene; and 5H-benzocycloheptene. When a hetereoatom, O or S, is present in A, examples include: 7-oxo-bicyclo[4.2.0]octa-1,3,5-triene; dihydrobenzofuran; dihydrogenzothiaphene; chroman; isochroman; thiochroman; tetrahydrobenzoxepin; and tetrahydrothiepin.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferably, A is a 5 membered saturated ring which either contains no heteroatom or contains O as a heteroatom. When A is a 5 membered saturated ring which contains no heteroatom, preferably, $R^3$ is preferably phenyl which is unsubstituted or substituted by methyl, methoxy, or chloro and $R^4$ is preferably hydrogen or methyl. Also preferable is when each of $R^1$ and $R^2$ is hydrogen. Also preferable is when $R^2$ and $R^5$ together with the carbon atoms to which they are bound form a phenyl ring. When A is a 5 membered ring which contains as a heteroatom, it is preferable that each of $R^1$ and $R^2$ is hydrogen and $R^3$ is preferably phenyl which is unsubstituted.

When A is a 6 membered saturated ring which contains no heteroatom, preferably, each of $R^1$ and $R^2$ is independently hydrogen, halogen, methyl, or methoxy, $R^3$ is preferably phenyl which is unsubstituted, $R^4$ is hydrogen, methyl, (2-oxo-2-phenyl-ethyl, 4,4,4-trifluoro-3-hydroxy-butyl, 2-hydroxy-ethyl, methoxymethyl, allyl, benzyl, ethyl, Acetyl, acetic acid methylester, and malonic acid dimethyl ester, or $R^2$ and $R^5$ together with the carbon atoms to which they are bound form either a saturated 6 membered ring (cyclohexyl) or an unsaturated 6 membered ring (phenyl).

When A is a 6 membered saturated ring which contains either O or S as a heteroatom, preferably each of $R^1$ and $R^2$ is independently hydrogen or halogen and $R^3$ is preferably phenyl which is unsubstituted.

When A is a 7 membered saturated ring, preferably it contains no heteroatom and each of $R^1$ and $R^2$ is hydrogen and $R^3$ is preferably phenyl which is unsubstituted and $R^5$ and $R^6$ together with the carbon atoms to which they are bound form either a saturated 6 membered ring (cyclohexyl) or an unsaturated 6 membered ring (phenyl).

Examples of preferred compounds in accordance with the above include:

8-(8-Chloro-1,2,3,4-tetrahydro-2-naphthyl)-1-phenyl-1,3,8-triaza-spiro[4.5]decan-4-one 8-(5,8-Dichloro-1,2,3,4-tetrahydro-2-naphthyl)-3-methyl-1-phenyl-1,3,8-triaza-spiro[4.5]decan-4-one 8-(5,8-Dichloro-1,2,3,4-tetrahydro-2-naphthyl)-3-ethyl-1-phenyl-1,3,8-triaza-spiro[4.5]decan-4-one 1-Phenyl-8-(1,2,3,4-tetrahydro-1-naphthyl)-1,3,8-triaza-spiro[4.5]decan-4-one

[8-(5,8-Dichloro-1,2,3,4-tetrahydro-2-naphthyl)-4-oxo-1-phenyl-1,3,8-triaza-spiro[4.5]dec-3-yl]-aceticacid methylester (−)-8-(5,8-Dichloro-1,2,3,4-tetrahydro-2-naphthyl)-1-phenyl-1,3,8-triaza-spiro[4.5]decan-4-one 8-Indan-2-yl-1-phenyl-1,3,8-triaza-spiro[4.5]decan-4-one (RS)-8-(Acenaphthen-1-yl)-1-phenyl-1,3,8-triaza-spiro[4.5]decan-4-one (RS)-8-(Acenaphthen-1-yl)-3-methyl-1-phenyl-1,3,8-triaza-spiro[4.5]decan-4-one (RS)-8-(2,3-Dihydro-1H-phenalen-1-yl)-1-phenyl-1,3,8-triaza-spiro[4.5]decan-4-one (R)-8-(Acenaphthen-1-yl)-1-phenyl-1,3,8-tniaza-spiro[4.5]decan-4-one 8-(2,3,3a,4,5,6-Hexahydro-1H-phenalen-1-yl)-1-phenyl-1,3,8-triaza-spiro[4.5]decan-4-one (RS)-8-(5-Methyl-1,2,3,4-tetrahydro-naphthalen-1-yl)-1-phenyl-1,3,8-triaza-spiro[4.5]decan-4-one The present compounds of formula I and their pharmaceutically acceptable salts can be prepared by methods known in the art, for example, by processes described below, which comprise a) hydrogenating the double bond in a compound of formula

II

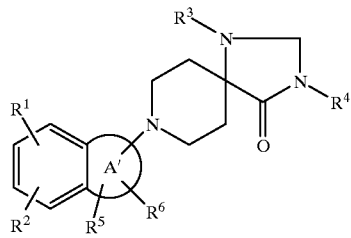

wherein $R^1$–$R^6$ are as defined above and A' is a 5–7 membered partial unsaturated ring which optionally contains a heteroatom selected from O or to a compound of formula I, or b) alkylating, benzylating or acylating a compound of formula I, wherein $R^4$ is hydrogen, to a compound of formula I, wherein $R^4$ lower alkyl, lower alkenyl, —C(O)-lower alkyl, —C(O)-phenyl, lower alkyl-C(O)-phenyl, lower alkylene-C(O)O-lower alkyl, lower alkantriyl-di-C(O)O-lower alkyl, hydroxy-lower alkyl, lower alkyl-O-lower alkyl, lower alkyl-CH(OH)CF$_3$, phenyl or benzyl, or c) reductively aminating a compound of formula

II

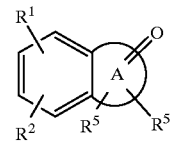

with a compound of formula

IV

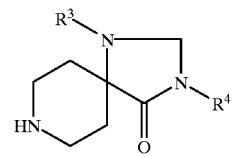

to a compound of formula

I

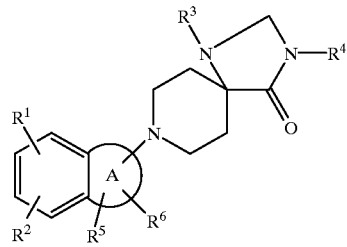

wherein A and $R^1$ $R^6$ are as defined above, or d) converting a racemic mixture into its enantiomeric components to obtain the optically pure compounds, and e) if desired, converting the compound of formula I obtained into a pharmaceutically acceptable acid addition salt.

In accordance with process variant a) a compound of formula II can be hydrogenated in conventional manner, for example with metal hydrides, such as borohydride, sodium cyanoborohyride or with triethylsilane in protic solvents, e.g. methanol or ethanol, and/or in the presence of protic reagents like trifluoroacetic acid in methylene chloride. This reaction is usually carried out at room temperature.

Another method is the hydrogenation in tile presence of at least one hydrogenating catalyst, such as palladium on carbon, platinum or ruthenium, in an inert solvent, for example methanol, ethanol or ethyl acetate or mixtures thereof. This reaction is carried out at a pressure of 1–1000 atmospheres and temperatures between 25 and 250° C.

In accordance with process variant b) a compound of formula I, wherein $R^4$ is hydrogen, can be alkylated, benzylated or acylated in conventional manner, for example in the presence of a corresponding alkyl-, benzyl- or acyl-halogenide, such as methyliodide, allylbromide, benzylbromide, ethylbromide, acetylchloride, methylbromacetate and the like. This reaction is carried out in the presence of a metal hydride, such as sodium hydride at a temperature of about 60–100° C.

The reductive amination of a keto-compound of formula III with an amine of formula IV in accordance with variant c) is carried out in conventional manner in a solvent, such as tetrahydrofuran (THF), methanol or ethanol, or in a mixture of THF with a suitable alcohol, and in the presence of a reducing agent, such as Na-cyanoborohydride.

Another method is described in J. Org. Chem., 55, 2552–54, 1990. In accordance with this variant the reaction is carried out by reaction of an amine with a ketone in the presence of TI-(IV)-isopropoxide and Na-cyanoborohydride.

The salt formation in accordance with variant e) is effected at room temperature in accordance with methods which are known per se and which are familiar to any person skilled in the art. Not only salts with inorganic acids, but also salts with organic acids come into consideration. Hydrochlorides, hydrobromides, sulfates, nitrates, citrates, acetates, maleates, succinates, methanesulphonates, p-toluenesulphonates and the like are examples of such salts.

The compounds which are used as starting materials can be prepared, for example, according to reaction schemes 1 and 2 and to Examples aa–av.

Furthermore, the starting materials of the(compound described in example 44 can be prepared in accordance with J. Org. Chem., 1995, 60, 4324–4330 and with J. Med. Chem., 1996, 39, 3169.

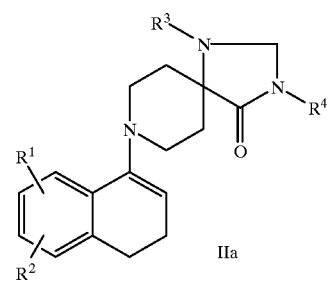

Scheme 1

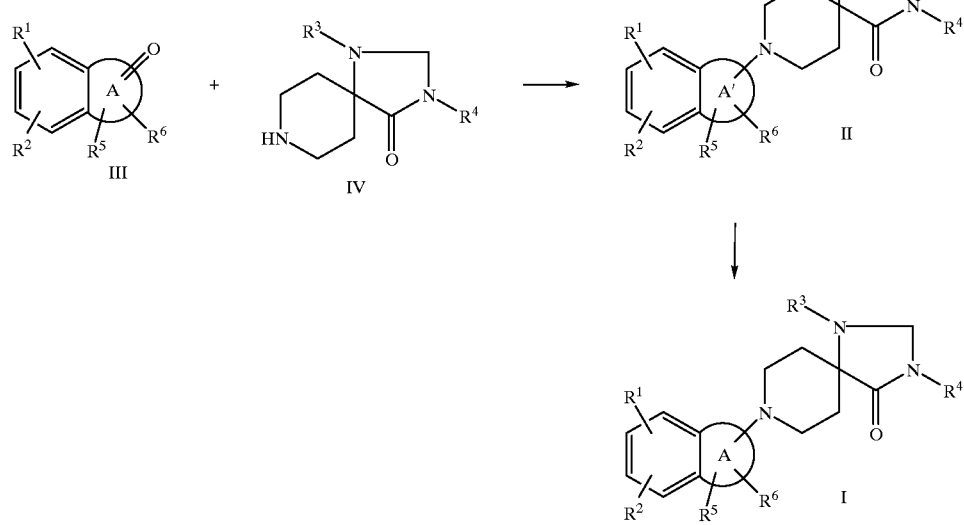

wherein the substituents are as defined above.

Scheme 2

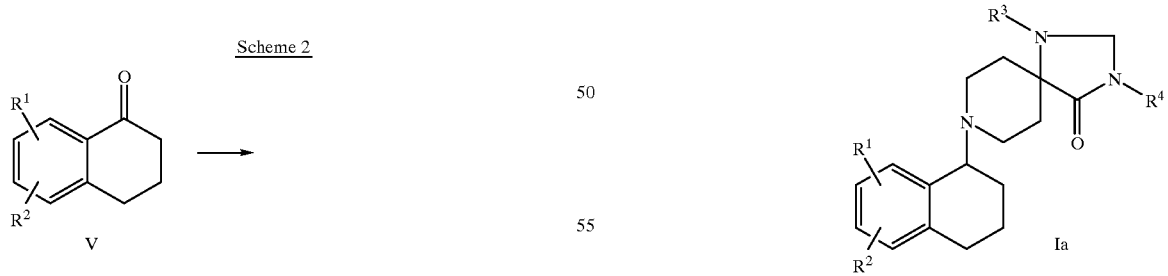

wherein the substituents are as defined above.

A compound of formula II is obtained by treating a suitable ketone of formula III with a secondary amine to an enamine with loss of water. This reaction is reversible, so water has to be removed azeotropically or with a drying agent. This reaction is carried out in an inert solvent, such as benzene or toluene and in the presence of an acidic catalyst like p-toluene sulfonic acid or sulfuric acid or, alternatively, with a drying agent, for example with molecular sieves at temperatures of about 80–120° C.

The above mentioned compounds of formula II can also be prepared by stirring components in an inert solvent, such as hexane, benzene or 1,2-dichloroethane at room temperature or elevated temperatures up to 80° C. in the presence of, e.g. titanium tetrachloride as Lewis-acid and drying agent. Compounds of formula I can then be obtained in accordance with process variant a).

In accordance with scheme 2 are obtained compounds of formula IIa. A compound of formula V is dissolved in an inert solvent, such as methanol, ethanol, water or mixtures thereof and refluxed with $NH_2OH$ and NaOAc. The obtained oxime is dissolved in an inert solvent such as diethylether. After a reaction with $NaNO_2$ in water in the presence of $H_2SO_4$ it is obtained a compound of formula VI. This compound is dissolved in an inert solvent, such as acetonitrile and stirred together with the co-responding compound of formula IV and molecular sieves to give a compound of formula IIa.

A compound of formula Ia can then be obtained by hydrogenation in accordance with process variant a).

The ketones or aldehydes of formulae III and V and the compounds of formula IV are known compounds or can be prepared according to methods known per se.

As mentioned earlier, the compounds of formula I, racemates and enantiomers thereof, and their pharmaceutically useable addition salts possess valuable pharmacodynamic properties. It has been found that the compounds of the present invention are agonists and/or antagonists of the OFQ receptor and have effects in animal models of psychiatric, neurological and physiological disorders, such as anxiety, stress disorders, depression, trauma, memory loss due to Alzheimer's disease or other dementias, epilepsy and convulsions, acute and/or chronic pain conditions, symptoms of withdrawal from drugs of addiction, control of water balance, $Na^+$ excretion, arterial blood pressure disorders and eating disorders such as obesity.

The compounds were investigated in accordance with the tests given hereinafter:

Methods of OFQ-R Binding Assay

Cell Culture

HEK-293 cells adapted to suspension growth (293s) were cultured in HL medium plus 2% FBS. The cells were transfected with the rat OFQ receptor cDNA (LC132), FEBS Lett. 347, 284–288, 1994, cloned in the expression vector pCEP4 (Invitrogen, San Diego, Calif., USA) using lipofectin (Life Technologies, Bethesda, Md., USA). Transfected cells were selected in the presence of hygromycin (1000 U/ml) (Calbiochem, San Diego, Calif., USA). A pool of resistant cells was tested for OFQ-R expression by binding of [$^3$H]-OFQ (Amersham PLC, Buckinghamshire, England). These cells (293s-OFQ-R) were expanded for large scale culture and membrane preparation.

Membrane Preparation

293s-OFQ-R cells were harvested by centrifugation, washed 3 times with phosphate buffered saline (PBS) before resuspension in buffer A (50 mM Tris-HCl, pH 7.8, 5 mM $MgCl_2$, 1 mM EGTA) and disruption with a tissue homogenizer (30 seconds, setting 4, Pt 20, Kinematica, Kriens-Lucern, Switzerland). A total membrane fraction was obtained by centrifugation at 49,000× g at 4° C. This procedure was repeated twice and the pellet was resuspended in buffer A. Aliquots were stored at −70° C. and protein concentrations were determined using the BCA™ Protein Assay Reagent (Pierce, Rockford, Ill.) following the manufacturer's recommendations.

Binding Assays

[$^3$H]-OFQ competition studies were carried out with 77 μg membrane protein in a final assay volume of 0.5 ml buffer A plus 0.1% BSA and 0.01% bacitracin (Boehringer-Mannheim, Mannheim, Germany) for one hour at room temperature. 50 nM unlabeled OFQ was used to define the non-specific binding. The assays were terminated by filtration through Whatman GF/C filters (Unifilter-96, Canberra Packard S.A., Zurich, Switzerland) pretreated with 0.3% polyethylenimine (Sigma, St. Louis, Mo., USA) and 0.1% BSA (Sigma) for 1 hour. The filters were washed 6 times with 1 ml of ice bold 50 mM Tris-HCl pH 7.5. The retained radioactivity was counted on a Packard Top-Count microplate scintillation counter after addition of 40 μl of Microscint 40 (Canberra Packard). The effects of compounds were determined using at least 6 concentrations in triplicate, and determined twice. $IC_{50}$ values were determined by curve fitting and these values were converted to $K_i$ values by the method of Cheng and Prusoff, Biochem. Pharmacol., 22, 3099, 1973.

The affinity to the OFQ-receptor, given as $pK_i$, is in the range of 6.6 to 9.6. For example, the $pK_i$ values of Examples 8 and 15 are 7.9 and 8.0, respectively.

Example 8: 3-Benzyl-8-(5,8-dichloro-1,2,3,4-tetrahydro-2-naphthyl)-1-phenyl-1,3,8-triaza-spiro[4,5]decan-4-one Example 15: 3-Acetyl-8-(5,8-dichloro-1,2,3,4-tetrahydro-2-naphthyl)-1-phenyl-1,3,8-triaza-spiro[4,5]decan-4-one The compounds of formula I, their racemates and enantiomers thereof, as; well as their pharmaceutically usable acid addition salts can be used as medicaments, e.g. in the form of pharmaceutical preparations. The pharmaceutical preparations can be administered orally, e.g. in the form of tablets, coated tablets, dragees, hard and soft gelatin capsules, solutions, emulsions or suspensions. The administration can, however, also be effected rectally, e.g. in the form of suppositories, or parenterally, e.g. in the form of injection solutions.

The compounds of formula I, their racemates and enantiomers thereof, and their pharmaceutically usable acid addition salts can be processed with pharmaceutically inert, inorganic or organic excipients for the production of tablets, coated tablets, dragees and hard gelatin capsules. Lactose, corn starch or derivatives thereof, talc, stearic acid or its salts etc. can be used as such excipients e.g. for tablets, dragees and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when it appears to be indicated.

The following Examples illustrate the present invention, but are not intended to be limiting in any manner. All temperatures are given in degrees Celsius.

EXAMPLE 1

8-(6-Chloro-1,2,3,4-tetrahydro-2-naphthyl)-1-phenyl-1,3,8-triaza-spiro[4.5]decan-4-one hydrochloride 6-Chloro-2-tetralone (22.7 mmol) was dissolved in toluene (210 ml). 1-Phenyl-1,3,8-triazaspiro[4.5]decan-4-one (22.7 mmol) and molecular sieves (10 g) were added and the mixture was refluxed for 6 h. After cooling the molecular sieves were removed by filtration and washed with methylene chloride. Evaporation of the filtrate yielded a residue which was dissolved in THF (90 ml) and methanol (10 ml). Sodium cyanoborohydride (22.7 mmol) was added to the solution and the pH was adjusted to 4. The mixture was stirred for 4 h at room temperature. Ethyl acetate was added and the organic phase was washed with 2 N sodium hydroxide and brine. The organic phase was concentrated and chromatographed over silica gel (ethyl acetate). Addition of HCl in ethanol to a solution of the product in ethyl acetate/ethanol yielded 8-(6-chloro-1,2,3,4-tetrahydro-2-naphthyl)-1-phenyl-1,3,8-triaza--spiro[4.5]decan-4-one hydrochloride (4.0 g, 41%) as colorless solid, m.p. 288–290° C.

EXAMPLE 2

8-(8-Chloro-1,2,3,4-tetrahydro-2-naphthyl)-1-phenyl-1,3,8-triaza-spiro[4.5]decan-4 -one hydrochloride The title compound, m.p. 286–290° C. was prepared in accordance with the general method of example 1 from 8-chloro-2-tetralone and 1-phenyl-1,3,8-triazaspiro[4.5]decan-4-one.

EXAMPLE 3

8-(5,8-Dichloro-1,2,3,4-tetrahydro-2-naphthyl)-1-phenyl-1,3,8-triaza-spiro[4.5]decan-4-one hydrochloride The title compound, m.p. 290–293° C. was prepared in accordance with the general method of example 1 from 5,8-dichloro-2-tetralone and 1-phenyl-1,3,8-triazaspiro[4.5]decan-4-one.

EXAMPLE 4

8-(6-Chloro-1,2,3,4tetrahydro-2-naphthyl)-3-methyl-1-phenyl-1,3,8-triaza-spiro[4.5]decan-4-one hydrochloride A suspension of 8-(6-chloro-1,2,3,4-tetrahydro-naphthyl-2)-1-phenyl-1,3,8-triaza-spiro[4.5]decan-4-one hydrochloride (0.47 mmol) and sodium hydride (60 mg, 60%) in DMF was stirred for 30 min. at 80° C. Methyl iodide (40 ml, 0.47 mmol) was added and stirring continued for another 30 min. The mixture was cooled, ethyl acetate (100 ml) was added and washed with sodium bicarbonate solution and brine (50 ml each). Water phases were extracted with ethyl acetate, organic phases were pooled, dried with sodium sulfate and evaporated. Addition of HCl in ethanol to a solution of the residue in ethyl acetate yielded 8-(6-chloro-1,2,3,4-tetrahydro-2-naphthyl)-3-methyl-1-phenyl-1,3,8-triaza-spiro[4.5]decan-4-one hydrochloride (0.17 g, 82%) as colorless solid, m.p.>250° C. and MS: m/e=410.2 (M+H$^+$).

EXAMPLE 5

8-(8-Chloro-1,2,3,4-tetrahydro-2-naphthyl)-3-methyl-1-phenyl-1,3.8-triaza-spiro[4.5]decan-4-one hydrochloride The title compound, m.p.>250° C. and MS: m/e=410.4 (M+H$^+$) was prepared in accordance with the general method of example 4 from 8-(8-chloro-1,2,3,4-tetrahydro-2-naphthyl-1-phenyl-1,3,8-triaza-spiro[4.5]decan-4-one and methyl iodide.

EXAMPLE 6

8-(5,8-Dichloro-1,2,3,4-tetrahydro-2-naphthyl)-3-methyl-1-phenyl-1,3,8-triaza-spir[4.5]decan-4-one hydrochloride The title compound, m.p.>250 ° C and MS: m/e=444.7, 446.6 (M+H$^+$) was prepared in accordance with the general method of example 4 from 8-(5,8-dichloro-1,2,3,4-tetrahydro-2-naphthyl)-1-phenyl-1,3,8-triaza-spiro[4.5]decan-4-one and methyl iodide.

EXAMPLE 7

3-Allyl-8-(5,8-dichloro-1,2,3,4-tetrahydro-2-naphthyl)-1-phenyl-1,3,8-triaza-spiro[4.5]decan-4-one hydrochloride The title compound, m.p.>250° C. and MS: m/e=470.4, 472.4 (M+H$^+$) was prepared in accordance with the general method of example 4 from 8-(5,8-dichloro-1,2,3,4-tetrahydro-2-naphthyl)-1-phenyl-1,3,8-triaza-spiro[4.5]decan-4-one and allyl bromide.

EXAMPLE 8

3-Benzyl-8-(5,8-dichloro-1,2,3,4-tetrahydro-2-naphthyl)-1-phenyl-1,3,8-triaza-spiro[4.5]decan-4-one hydrochloride The title compound, m.p.>250° C. and MS: m/e=520.3, 522.3 (M+H$^+$) was prepared in accordance with the general method of example 4 from 8-(5,8-dichloro-1,2,3,4-tetrahydro-2-naphthyl)-1-phenyl-1,3,8-triaza-spiro[4.5]decan-4-one and benzyl bromide.

EXAMPLE 9

8-(5,8-Dichloro-1,2,3,4-tetrahydro-2-naphthyl)-3-ethyl-1-phenyl-1,3,8-triaza-spiro[4.5]decan-4-one hydrochloride The title compound, m.p.>250° C. and MS: m/e=458.3, 460.3 (M+H$^+$) was prepared in accordance with general method of example 4 from 8-(5,8-dichloro-1,2,3,4-tetrahydro-2-naphthyl)-1-phenyl-1,3,8-triaza-spiro[4.5]decan-4-one and ethyl bromide.

EXAMPLE 10

1-Phenyl-8-(1,2,3,4-tetrahydro-2-naphthyl)-1,3,8-triaza-spiro[4.5]decan-4-one hydrochloride The title compound, m.p.>250° C. and MS: m/e=362.3 (M+H$^+$) was prepared in accordance with general method of example 1 from 2-tetralone and 1-phenyl-1,3,8-triazaspiro[4.5]decan-4-one.

EXAMPLE 11

1-Phenyl-8-(1,2,3,4-tetrahydro-1-triaza-spiro[4.5]decan-4-one hydrochloride 3,4-Dihydro-2H-naphthyl-1-oxime (2.98 mmol) was dissolved in ether (6 ml.) and a solution of sodium nitrite (5 mmol) in 2,5 ml water was added. The solution was stirred for 1 hr under inert atmosphere (Ar). Then 1N H$_2$SO$_4$ (5 ml) was added and the solution was stirred for 3 hrs. The organic phase was separated and washed twice with 5 ml NaHCO$_3$. The water phase was washed with 5 ml ether. Evaporation of the pooled orgaalic phases yielded a residue which was dissolved in acetonitril (10 ml) and to this solution was added at 0° C. a suspension of 1-phenyl-1,3,8-triaza-spiro [4.5]-decan-4-one (11.9 mmnol) in acetonitril (30 ml). The mixture and molecular sieves (10 g) were stirred about 40 hrs at room temperature in inert atmosphere (Ar). The organic phase was concentrated and washed twice with acetonitril (20 ml). After evaporation of the filtrate the residue was dissolved in THF (90 ml) and ethanol (10 ml). Sodium cyanoborohydride (190 mg) was added to the solution and the pH was adjusted to 4 (HCl/EtOH). The mixture was stirred for 105 min. at room temperature. Evaporation and purification (described in example 1) yielded 1-phenyl-8-(1,2,3,4-tetrahydro-1-naphthyl)-1,3,8-triaza-spiro[4.5] decan-4-one hydrochloride, m.p.>250° C. and MS: m/e=361 (M$^+$).

EXAMPLE 12
8-(7-Chloro-1,2,3,4-tetrahydro-2-naphthyl)-1-phenyl-1,3,8-triaza-spiro[45]decan-4-one hydrochloride The title compound, m.p.>250° C. and MS: m/e=396.2, 398.2 (M+H$^+$) was prepared in accordance with general method of example 1 from 7-chloro-2-tetralone and 1-phenyl-1,3,8-triaza-spiro[4.5]decan-4-one.

EXAMPLE 13
8-(5-Chloro-1,2,3,4-tetrahydro-2-naphthyl)-1-phenyl-1,3,8-triaza-spiro[4.5]decan-4-one hydrochloride The title compound, m.p.>250° C. and MS: m/e=396.4, 398.4 (M+H$^+$) was prepared in accordance with general method of example 1 from 5-chloro-2-tetralone and 1-phenyl-1,3,8-triaza-spiro[4.5]decan-4-one.

EXAMPLE 14
8-(5,7-Dimethyl-1,2,3,4-tetrahydro-2-naphthyl)-1-phenyl-1,3,8-triaza-spiro[4.5]decan-4-one hydrochloride The title compound, m.p.>250° C. and MS: m/e=389 (M$^+$) was prepared in accordance with general method of example 1 from 5,7-dimethyl-2-tetralone and 1-phenyl-1,3,8-triazaspiro[4.5]decan-4-one.

EXAMPLE 15
3-Acetyl-8-(5,8-dichloro-1,2,3,4-tetrahydro-2-naphthvyl-1-phenyl-1,3,8-triaza-spiro[4.5]decan-4-one hydrochloride The title compound, m.p.>250° C. and MS: m/e=472.3, 474.4 (M+H$^+$) was prepared in accordance with general method of example 4 from 8-(5,8-dichlor- 1,2,3,4-tetrahydro-2-naphthyl)-1-phenyl-1,3,8-triaza-spiro[4.5]decan-4-one and acetyl chloride.

EXAMPLE 16
[8-(5,8-Dichloro-1,2,3,4-tetrahydro-2-naphthyl)-4-oxo-1-phenyl-1,3,8-triaza-spiro[4.5]dec-3-yl]-acetic acid methylester dydrcchloride The title compound, m.p. 185–187° C. was prepared in accordance with the general method of example 4 from 8-(5,8-dichloro-1,2,3,4-tetrahydro-2-naphthyl)-1-phenyl-1,3,8-triaza-spiro[4.5]decan-4-one and methyl bromoacetate.

EXAMPLE 17
(−)-8-(5,8-Dichloro-1,2,3,4-tetrahydro-2-naphthyl)-1-phenyl-1,3,8-triaza-spiro[4.5]decan-4-one hydrochloride The title compound, m.p.>250° C., MS: m/e=430.5, 432.5 (M+H$^+$) and [α]=−54.9 was prepared from 8-(5,8-dichloro-1,2,3,4tetrahydro-2-naphthyl)-1-phenyl-1,3,8-triaza-spiro[4.5]decan-4-one by cocrystallization with (+)-2,2'-(1,1'-binaphthyl)-phosphoric acid.

EXAMPLE 18
(+)-8-(5,8-Dichloro-1,2,3,4-tetrahydro-2-naphthyl)-1-phenyl-1,3,8-triaza-spiro[4.5]decan-4-one hydrochloride The title compound, m.p.>250° C., MS: m/e=430.5, 432.5 (M+H$^+$) and [α]=+53.2 was prepared from 8-(5,8-dichloro-1,2,3,4-tetrahydro-2-naphthyl)-1-phenyl-1,3,8-triaza-spiro[4.5]decan-4-one by cocrystallization with (−)-2,2'-(1,1'-binaphthyl)-phosphoric acid.

EXAMPLE 19
(RS)-3-Benzoyl-8-(5,8-dichloro-1,2,3,4-tetrahydro-naphthalen-2-yl)-1-phenyl-1,3,8-triaza-spiro[4.5]decan-4-one hydrochloride (1:1)

The title compound, m.p. 220° C. dec. was prepared in accordance with the general method of example 4 from 8-(5,8-dichloro-1,2,3,4-tetrahydro-2 -naphthyl)-1-phenyl-1,3,8-triazaspiro[4.5]decan-4-one hydrochloride and benzoyl chloride.

EXAMPLE 20
(RS)-2-[8-(5,8-Dichloro-1,2,3,4-tetrahydro-naphtlalen-2-yl)-4-oxo-1-phenyl-1,3,8-triaza-spiro[4.5]dec-3-yl]-malonic acid dimethyl ester hydrochloride (1:1)

The title compound, m.p. 191–192° C. dec. was prepared in accordance with the general method of example 4 from 8-(5,8-dichloro-1,2,3,4-tetrahydro-2-naphthyl)-1-phenyl-1,3,8-triazaspiro[4.5]decan-4-one hydrochloride and dimethyl bromomalonate.

EXAMPLE 21
(RS)-8-(8-Chloro-1,2,3,4-tetrahydro-naphthalen-2-yl)-3-(2-oxo-2-phenyl-ethyl)-1-phenyl-1,3,8-triaza-spiro[4.5]decan-4-one hydrochloride (1:1)

The title compound, m.p.>250° C. and MS: m/e=514.3 (M+H$^+$) was prepared in accordance with the general method of example, 4 from 8-(8-Chloro-1,2,3,4-tetrahydro-2-naphthyl)-1-phenyl-1,3,8-triazaspiro[4.5]decan-4-one hydrochloride and phenacyl bromide.

EXAMPLE 22
(RS)-8-(5,8-Dimethyl-1,2,3,4-tetrahydro-naphthalen-2-yl)-1-phenyl-1,3,8-triaza-spiro[4.5]decan-4-one hydrochloride (1:1)

The title compound, m.p.>250° C. and MS: m/e=390.5 (M+H$^+$) was prepared in accordance with the general method of example 1 from 3,4-dihydro-5,8-dimethyl-1(2H)-naphthalenone and 1-phenyl-1,3,8-triazaspiro[4.5]decan-4-one.

EXAMPLE 23
(RS)-8-(8-Chloro-1,2,3,4-tetrahydro-naphthalen-2-yl)-3-(2-dydroxy-ethyl)-1-phenyl-1,3,8-triaza-spiro[4.5]decan-4-one hydrochloride (1:1)

The title compound, m.p. 244° C. dec. and MS: m/e=439 (M$^+$) was prepared in accordance with the general method of example 4 from 8-(8-Chloro-1,2,3,4 -tetrahydro-2-naphthyl)-1-phenyl-1,3,8-triazaspiro[4.5]decan-4-one hydrochloride and 2-chloroethoxy-trimethylsilane (in situ deprotection).

EXAMPLE 24
(RS)-8-(8-Chloro-1,2,3,4-tetrahydro-naphthaler,-2-yl)-3-methoxymethyl-1-phenyl-1,3,8-triaza-spiro[4.5]decan-4-one hydrochloride (1:1)

The title compound, m.p.>227–229° C. dec. and MS: m/e=440.6 (M+H$^+$) was prepared in accordance with the general method of example 4 from 8-(8-Chloro-1,2,3,4-tetrahydro-2-naphthyl)-1-phenyl-1,3,8-triazaspiro[4.5]decan-4-one hydrochloride and chloromethyl-methylether.

EXAMPLE 25
Mixture of 1-phenyl-8-[(R)- and [(S)-1,2,3,4-tetrahydro-naphthalen-2-yl]-3-[(S)-4,4,4-trifluoro-3-hydroxy-butyl]-1,3,8-triaza-spiro[4.5]decan-4-one hydrochloride (1:1)

The title compound mixture, m.p.>245° C. dec. and MS: m/e=488.5 (M+H$^+$) was prepared in accordance with the general method of example 4 from 8-(1,2,3,4-tetrahydro-2-naphthyl)-1-phenyl-1,3,8-triazaspiro[4.5]decan-4-one hydrochloride and (S)-1-(4-methylbenzenesulfonate)-4,4,4-trifluoro-1,3-butanediol.

EXAMPLE 26
(RS)-8-Indan-1-yl-1-phenyl-1,3,8-triaza-spiro[4.5]decan-Lone hydrochloride (1:1)

The title compound, m.p.>250° C. and MS: m/e=348.4 (M+H$^+$) was prepared in accordance with the general method of example 11 from 2,3-dihydro-1H-inden-1-one oxime and 1-phenyl-1,3,8-triazaspiro[4.5]decan-4-one.

EXAMPLE 27
Mixture of 1-phenyl-8-[(R)- and -[(S)-1,2,3,4-tetrahydro-naphthalen-2-yl]-3-[(R)-4,4,4-trifluoro-3-hydroxy-butyl]-1,3,8-triaza-spiro[4.5]decan-4-one hydrochloride (1:1)

The title compound mixture, m.p.>246° C. dec. and MS: m/e=488.5 (M+H$^+$) was prepared in accordance with the general method of example 4 from 8-(1,2,3,4-tetrahydro-2-naphthyl)-1-phenyl-1,3,8-triazaspiro[4.5]decan-4-one hydrochloride and (R)-1-(4-methylbenzenesulfonate)-4,4,4-trifluoro-1,3-butanediol.

EXAMPLE 28
(RS)-8-(2,3-Dihydro-benzofuran-3-yl)-1-phenyl-1,3,8-triaza-spiro[4.5]decan-4-one hydrochloride (1:1)

The title compound, m.p.>235° C. dec. and MS: m/e=350.4 (M+H$^+$) was prepared in accordance with the general method of example 1 from 3(2H)-benzofuranone and 1-phenyl-1,3,8-triazaspiro[4.5]decan-4-one.

EXAMPLE 29
(RS)-8-(8-Bromo-1,2,3,4-tetrahydro-naphthalen-2-yl)-1-phenyl-1,3,8-triaza-spiro[4.5]decan-4-one hydrochloride (1:1)

The title compound, m.p.>250° C. dec. and MS: m/e=440.4, 442.4 (M+H$^+$) was prepared in accordance with the general method of example 1 from 8-bromo-3,4-dihydro-2(1H)-naphthalenone and 1-phenyl-1,3,8-triazaspiro[4.5]decan-4-one.

EXAMPLE 30
Mixture of (1RS,3RS)- and (1RS,3SR)-1-phenyl-8-(3-phenyl-indan-1-yl)-1,3,8-triaza-spiro[4.5]decan-4-one hydrochloride (1:1)

The title compound mixture, m.p.>250° C. and MS: m/e=424.4 (M+H$^+$) was prepared in accordance with the general method of example 1 from 2,3-dihydro-3-phenyl-1H-inden-1-one and 1-phenyl-1,3,8-triazaspiro[4.5]decan-4-one.

EXAMPLE 31
Mixture of (1RS,3RS)- and (1RS,3SR)-8-(3-methyl-indan-1-yl)-1-phenyl-1,3,8-triaza-spiro[4.5]decan-4-one hydrochloride (1:1)

The title compound mixture, m.p.>244–246° C. dec. and MS: m/e=361 (M$^+$) was prepared in accordance with the general method of example 1 from 2,3-dihydro-3-methyl-1H-inden-1-one and 1-phenyl-1,3,8-triazaspiro[4.5]decan-4-one.

EXAMPLE 32
8-Indan-2-yl-1-phenyl-1,3,8-triaza-spiro[4.5]decan-4-one hydrochloride (1:1)

The title compound, m.p.>250° C. and MS: m/e=348.4 (M+H$^+$) was prepared in accordance with the general method of example 1 from 1,3-dihydro-2H-inden-2-one and 1-phenyl-1,3,8-triazaspiro[4.5]decan-4-one.

EXAMPLE 33
(RS)-1-Phenyl-8-(3,3,6-trimethyl-indan-1-yl)-1,3,8-triaza-spiro[4.5]decan-4-one methanesulfonate (1:1)

The title compound, m.p. 250° C. and MS: m/e=390.2 (M+H$^+$) was prepared in accordance with the general method of example 1 from 2,3-dihydro-3,3,6-trimethyl-1H-inden-1-one and 1-phenyl-1,3,8-triazaspiro[4.5]decan-4-one.

EXAMPLE 34
(RS)-1-Phenyl-8-(6,7,8,9-tetrahydro-5H-benzocyclohepten-5-yl)-1,3,8-triaza-spiro[4.5]decan-4-one hydrochloride (1:1)

6,7,8,9-Tetrahydro-5H-benzocyclohepten-5-one (3.1 mmol) was dissolved in THF (10 ml). 1-Phenyl-1,3,8-triazaspiro[4.5]decan-4-one (3.1 mmol) and tetraisopropyl-orthotitanate (3.1 mmol) were added and the mixture was stirred for 22 h at room temperature. Evaporation yielded a residue which was dissolved in ethanol (5 ml). Sodium cyanoborohydride (2.1 mmol) was added to the solution and the mixture was stirred for 2 d at room temperature. Water was added, the precipitate was removed by filtration through Celite® and washed with ethanol. The filtrate was dried with Na$_2$SO$_4$ and concentrated. Chromatography on silica gel (ethyl acetate/hexane, 50:50) yielded the desired product which was crystallized as its HCl-salt from methylene chloride/ethanol. 0.1 g (8%) of (RS)-1-Phenyl-8-(6,7,8,9-tetrahydro-5H-benzocyclohepten-5-yl)-1,3,8-triaza-spiro[4.5]decan-4-one hydrochloride (1:1) as a colorless solid, m.p.>250° C. and MS: m/e=371.4 (M+H$^+$).

EXAMPLE 35
(RS)-8-(5-Chloro-1,2,3,4-tetrahydro-naphthalen-1-yl)-1-phenyl-1,3,8-triaza-spiro[4.5]decan-4-one hydrochloride (1:1)

The title compound, m.p.>250° C. and MS: m/e=396.2 (M+H$^+$) was prepared in accordance with the general method of example 11 from 5-chloro-3,4dihydro-1(2H)-naphthalenone oxime and 1-phenyl-1,3,8-triazaspiro[4.5]decan-4-one.

EXAMPLE 36
(RS)-8-(7-Fluoro-1,2,3,4-tetrahydro-naphthalen-1-yl)-1-phenyl-1,3,8-triaza-spiro[4.5]decan-4-one hydrochloride (1:1)

The title compound, m.p.>250° C. and MS: m/e=380.3 (M+H$^+$) was prepared in accordance with the general method of example 11 from 7-fluoro-3,4-dihydro-1(2H)-naphthalenone oxime and 1-phenyl-1,3,8-triazaspiro[4.5]decan-4-one.

EXAMPLE 37
(RS)-8-(5-Chloro-indan-1-yl)-1-phenyl-1,3,8-triaza-spiro[4.5]decan-4-one hydrochloride (1:1)

The title compound, m.p.>250° C. and MS: m/e=382.2 (M+H$^+$) was prepared in accordance with the general method of example 34 from 5-chloro-2,3-dihydro-1H-inden-1-one and 1-phenyl-1,3,8-triazaspiro[4.5]decan-4-one.

EXAMPLE 38
(RS)-8-(7-Chloro-5-fluoro-1,2,3,4-tetrahydro-naphthalen-1-yl)-1-phenyl-1,3,8-triaza-spiro[4.5]decan-4-one hydrochloride (1:1)

The title compound, m.p.>250° C. and MS: m/e=414.2 (M+H$^+$) was prepared in accordance with the general method of example 11 from 7-chloro-5-fluoro-3,4 -dihydro-1(2H)-naphthalenone oxime and 1-phenyl-1,3,8-triazaspiro[4.5]decan-4-one.

EXAMPLE 39
(RS)-8-(4-Methyl-indan-1-yl)-1-phenyl-1,3,8-triaza-spiro[4.5]decan-4-one hydrochloride (1:1)

The title compound, m.p.>250° C. and MS: m/e=362.2 (M+H$^+$) was prepared in accordance with the general method of example 34 from 2,3-dihydro-4methyl-1H-inden-1-one and 1-phenyl-1,3,8-triazaspiro[4.5]decan-4-one.

EXAMPLE 40
8-Indan-2-yl-3-methyl-1-phenyl-1,3,8-triaza-spiro[4.5]decan-4-one hydrochloride The title compound, m.p.>250° C. and MS: m/e=362.2 (M+H$^+$) was prepared in accordance with the general method of example 4 from 8-indan-2-yl-1-phenyl-1,3,8-triaza-spiro[4.5]decan-4-one hydrochloride (1:1) and methyl iodide.

EXAMPLE 41
(RS)-8-(7-Chloro-1,2,3,4-tetrahydro-naphthalen-1-yl)-1-phenyl-1,3,8-triaza-spiro[4.5]decan-4-one hydrochloride (1:1)

The title compound, m.p.>250° C. and MS: m/e=396.2 (M+H$^+$) was prepared in accordance with the general method of example 11 from 7-chloro-3,4-dihydro-1(2H)-naphthalenone oxime and 1-phenyl-1,3,8-triazaspiro[4.5]decan-4-one.

EXAMPLE 42
(RS)-3-Methyl-1-phenyl-8-(1,2,3,4-tetrahydro-naphthalen-1-yl)-1,3,8-triaza-spiro[4.5]decan-4-one hydrochloride (1:1)

The title compound, m.p. 232–234° C. was prepared in accordance with the general method of example 4 from 1-phenyl-8-(1,2,3,4-tetrahydro-1-naphthyl)-1,3,8-triaza-spiro[4.5]decan-4-one hydrochloride (1:1) and methyl iodide.

EXAMPLE 43
(RS)-8-Indan-1-yl-3-methyl-1-phenyl-1,3,8-triaza-spiro[4.5]decan-4-one hydrochloride (1:1)

The title compound, m.p. 200–203° C. and MS: m/e=362.2 (M+H$^+$) was prepared in accordance with the general method of example 4 from (RS)-8-indan-1-yl-1-phenyl-1,3,8-triaza-spiro[4.5]decan-4-one hydrochloride (1:1) and methyl iodide.

EXAMPLE 44
(R)-8-Indan-1-yl-1-phenyl-1,3,8-triaza-spiro[4. 5]decan-4-one hydrochloride (1:1)

(R)-1-Indan-1-yl-4-phenylamino-piperidine-4-carboxylic acid amide (2.9 mmol) suspended in formamide (15 ml) was stirred for 2 h at 200° C. The mixture was cooled, poured into cold water (150 ml) and extracted with methylene chloride. Organic phases were pooled, dried with sodium sulfate and concentrated to yield a mixture of (R)-8-indan-1-yl-1-phenyl-1,3,8-triaza-spiro[4.5]decan-4-one and (R)-8-indan-1-yl-1-phenyl-1,3,8-triaza-spiro[4.5]dec-2-en-4-one. This mixture was dissolved in methanol (60 ml) and sodium borohydride (4.2 mmol) was added. The mixture was stirred for 1 h at 60° C., cooled and concentrated. Saturated ammonium chloride solution and methylene chloride were added to the residue. The water phase was extracted with methylene chloride. Organic phases were pooled, dried with sodium sulfate and concentrated. Chromatography on silica gel (methylene chloride/methanol, 98:2) yielded the desired product. This was crystallized as its HCl-salt from ethyl acetate/ethanol. 0.27 g (24%) of (R)-8-indan-1-yl-1-phenyl-1,3,8-triaza-spiro[4.5]decan-4-one hydrochloride (1:1), m.p.>250° C. and MS: m/e=348.4 (M+H$^+$).

EXAMPLE 45
(RS)-8-(6-Chloro-thiochroman-4-yl)-1-phenyl-1,3,8-triaza-spiro[4.5]decan-4-one The title compound, m.p. 164–166° C. dec. and MS: m/e=414.2 (M+H$^+$) was prepared in accordance with the general method of example 11 from 6-chloro-2,3-dihydro-4H-1-benzothiopyran-4-one oxime and 1-phenyl-1,3,8-triazaspiro[4.5]decan-4-one.

EXAMPLE 46
(RS)-8-(6-Methoxy-1,2,3,4-tetrahydro-naphthalen-1-yl)-1-phenyl-1,3,8-triaza-spiro[4.5]decan-4-one hydrochloride (1:1)

The title compound, m.p. 235–236° C. and MS: m/e=392.2 (M+H$^+$) was prepared in accordance with the general method of example 11 from 3,4-dihydro-6-methoxy-1(2H)-naphthalenone oxime and 1-phenyl-1,3,8-triazaspiro[4.5]decarn-4-one.

EXAMPLE 47
(RS)-8-(5-Methoxy-1,2,3,4-tetrahydro-naphthalen-1-yl)-1-phenyl-1,3,8-triaza-spiro[4.5]decan-4-one hydrochloride (1:1)

The title compound, m.p.>250° C. and MS: m/e=392.3 (M+H$^+$) was prepared in accordance with the general method of example 11 from 3,4-dihydro-5-methoxy-1(2H)-naphthalenone oxime and 1-phenyl-1,3,8-triazaspiro[4.5]decan-4-one.

EXAMPLE 48
(S)-8-Indan-1-yl-1-phenyl-1,3,8-triaza-spiro[4.5]decan-4-one hydrochloride (1:1)

The title compound, m.p.>250° C. dec. and MS: m/e=348.4 (M+H$^+$) was prepared in accordance with the general method of example 44 from (S)-1-indan-1-yl-4-phenylamino-piperidine-4-carboxylic acid amide.

EXAMPLE 49
(RS)-8-(6-Chloro-1,2,3,4-tetrahydro-naphthalen-1-yl)-1-phenyl-1,3,8-triaza-spiro[4.5]decan-4-one hydrochloride (1:1)

The title compound, m.p.>250° C. and MS: m/e=396.2 (M+H$^+$) was prepared in accordance with the general method of example 11 from 6-chloro-3,4-dihydro-1(2H)-naphthalenone oxime and 1-phenyl-1,3,8-triazaspiro[4.5]decan-4-one.

EXAMPLE 50
1-Phenyl-8-(6,7,8,9-tetrahydro-5H-benzocyclohepten-7-yl)-1,3,8-triaza-spiro[4.5]decan-4-one hydrochloride (1:1)

The title compound, m.p.>250° C. and MS: m/e=376.3 (M+H +) was prepared in accordance with the general method of example 1 from 5,6,8,9-tetrahydro-7H-benzocyclohepten-7-one and 1-phenyl-1,3,8-triaz.ispiro[4.5]decan-4-one.

EXAMPLE 51
(RS)-8-(6-Fluoro-chroman-4-yl)-1-phenyl-1,3,8-triaza-sprio[4.5]decan-4-one hydrochloride (1:1)

The title compound, m.p.>250° C. and MS: m/e=382.2 (M+H$^+$) was prepared in accordance with the general method of example 11 from 6-fluoro-2,3-dihydro-4H-1-benzopyran-4-one oxime and 1-phenyl-1,3,8-triazaspiro[4.5]decan-4-one.

EXAMPLE 52
(RS)-8-(6-Chloro-chroman-4-yl)-1-phenyl-1,3,8-triaza-spiro[4.5]decan-4-one hydrochloride (1:1)

The title compound, m.p.>250° C. and MS: m/e=398.2 (M+H$^+$) was prepared in accordance with the general method of example 11 from 6-chloro-2,$^3$-dihydro-4H-1-benzopyran-4-one oxide and 1-phenyl-1,3,8-triazaspiro[4.5]decan-4-one.

EXAMPLE 53

(R)-1-Phenyl-8-(1,2,3,4-tetrahydro-naphthalen-1-yl)-1,3,8-triaza-spiro[4.5]decan-4-one hydrochloride (1:1)

The title compound, m.p.>250° C. and MS: m/e=362.2 (M+H$^+$) was prepared in accordance with the general method of example 44 from (R)-4-phenylamino-1-(1,2,3,4-tetrahydro-naphtalen-1-yl)-piperidine4-carboxylic acid amide.

EXAMPLE 54

(S)-1-Phenyl-8-(1,2,3,4-tetrahydro-naphthalen-1-yl)-1,3,8-triaza-sprio[4.5]decan-4-one hydrochloride (1:1)

The title compound, m.p.>250° C. and MS: m/e=362.2 (M+H$^+$) was prepared in accordance with the general method of example 44 from (S)-4-phenylamino-1-(1,2,3,4-tetrahydro-naphtalen-1-yl)-piperidine-4-carboxylic acid amide.

EXAMPLE 55

(RS)-8-(4-Chloro-indan-1-yl)-1-phenyl-1,3,8-triaza-spiro[4.5]decan-4-one hydrochloride (1:1)

The title compound, white solid, m.p.>230° C. and MS: m/e=382.2 (M+H$^+$) was prepared in accordance with the general method of example 34 from 4-chloro-indan-1-one and 1-phenyl-1,3,8-triazaspiro[4.5]decan-4-one.

EXAMPLE 56

(RS)-8-(Chroman-4-yl)-1-phenyl-1,3,8-triaza-spiro[4.5]decan-4-one hydrochloride (1:1)

The title compound, white solid, m.p. 240° C. (dec.) and MS: m/e=363 (M$^+$) was prepared in accordance with the general method of example 11 from 4-chromanone oxime and 1-phenyl-1,3,8-triazaspiro[4.5]decan-4-one.

EXAMPLE 57

(RS)-8-(5-Methoxy-indan-1-yl)-1-phenyl-1,3,8-triaza-spiro[4.5]decan-4-one hydrochloride (1:1)

The title compound, white solid, m.p.>220° C. and MS: m/e=378.3 (M+H$^+$) was prepared in accordance with the general method of example 34 from 5-methoxy-indan-1-one and 1-phenyl-1,3,8-triazaspiro[4.5]decan-4-one.

EXAMPLE 58

(RS)-8-(4-Methoxy-indan-1-yl)-1-phenyl-1,3,8-triaza-spiro[4.5]decan-4-one hydrochloride (1:1)

The title compound, light yellow solid, m.p.>220° C. and MS: m/e=378.3 (M+H$^+$) was prepared in accordance with the general method of example 34 from 4-methoxy-indan-1-one and 1-phenyl-1,3,8-triazaspiro[4.5]decan-4-one.

EXAMPLE 59

(RS)-8-(Acenaphthen-1-yl)-1-phenyl-1,3,8-triaza-spiro[4.5]decan-4-one hydrochloride (1:1)

The title compound, light yellow solid, m.p.>220° C. and MS: m/e=384.3 (M+H$^+$) was prepared in accordance with the general method of example 34 from 2H-acenaphthylen-1-one and 1-phenyl-1,3,8-triazaspiro[4.5]decan-4-one.

EXAMPLE 60

(RS)-8-(6-Methoxy-indan-1-yl)-1-phenyl-1,3,8-triaza-spiro[4.5]decan-4-one hydrochloride (1:1)

The title compound, light yellow solid, m.p.>220° C. and MS: m/e=378.3 (M+H$^+$) was prepared in accordance with the general method of example 34 from 5-methoxy-indan-1-one and 1-phenyl-1,3,8-triazaspiro[4.5]decan-4-one.

EXAMPLE 61

(RS)-8-(5-iso-Propyl-indan-1-yl)-1-phenyl-1,3,8-triaza-spiro[4.5]decan-4-one hydrochloride (1:1)

The title compound, off white solid m.p.>220° C. and MS: m/e=390.2 (M+H$^+$) was prepared in accordance with the general method of example 34 from 5-iso-propyl-indan-1-one and 1-phenyl-1,3,8-triazaspiro[4.5]decan-4-one.

EXAMPLE 62

8-(3-Phenyl-1,2,3,4-tetrahydro-naphthalen-1-yl)-1-phenyl-1,3,8-triaza-spiro[4.5]decan-4-one hydrochloride (1:1) (mixture of diast. racemates)

The title compound mixture, white solid, m.p. 203° C. and MS: m/e=438.3 (M+H$^+$) was prepared in accordance with the general method of example 11 from 3-phenyl-3,4-dihydro-1(2H)-naphthalenone oxime and 1-phenyl-1,3,8-triazaspiro[4.5]decan-4-one.

EXAMPLE 63

(RS)-8-(7-Methoxy -1,2,3,4-tetrahydro-naphthalen-1-yl)-1-phenyl-1,3,8-triaza-spiro[4.5]decan-4-one hydrochloride (1:1)

The title compound, white solid, m.p.>220° C. and MS: m/e=392.2 (M+H$^+$) was prepared in accordance with the general method of example 11 from 7-methoxy-3,4-dihydro-1(2H)-naphthalenone oxime and 1-phenyl-1,3,8-triazaspiro[4.5]decan-4-one.

EXAMPLE 64

(RS)-8-(Acenaphthen-1-yl)-3-methyl-1-phenyl-1,3,8-triaza-spiro[4.5]decan-4-one hydrochloride (1:1)

The title compound, light brown solid, m.p.>185° C. (dec.) and MS: m/e=398.3 (M+H$^+$) was prepared in accordance with the general method of example 4 from (RS)-8-(acenaphthen-1-yl)-1-phenyl-1,3,8-triazaspiro[4.5]decan-4-one hydrochloride (1:1) and methyl iodide.

EXAMPLE 65

8-(6,7-Dihydro-5H-dibenzo[a.c]cyclo-hepten-6-yl)-1-phenyl-1,3,8-triaza-spiro[4.5]decan-4-one hydrochloride (1:1)

The title compound, white solid, m.p.>220° C. and MS: m/e=424.3 (M+H$^+$) was prepared in accordance with the general method of example 1 from 5,7 -dihydro-dibenzo[a,c]cyclo-hepten-6-one and 1-phenyl-1,3,8-triazaspiro[4.5]decan-4-one.

EXAMPLE 66

8-(1,2,2a,3,4,5-Hexahydro-acenaphthylen-1-yl)-1-phenyl-1,3,8-triaza-spiro[4.5]decan-4-one hydrochloride (1:1) (mixture of diast. racemates)

The title compound mixture, light brown solid, m.p. 293° C. (dec.) and MS: m/e=388.2 (M+H$^+$) was prepared in accordance with the general method of example 34 from 2a,3,4,5-tetrahydro-2H-acenaphthylen-1-one and 1-phenyl-1,3,8-triazaspiro[4.5]decan-4-one.

EXAMPLE 67

(RS)-8-(2,3-Dihydro-1H-phenalen-1-yl)-1-phenyl -1,3,8-triaza-spiro[4.5]decan-4-one hydrochloride (1:1)

The title compound, light brown solid, m.p. 251° C. and MS: m/e=398.3 (M+H$^+$) was prepared in accordance with the general methods of example aa and 44 from 4-phenylamino-1-(2,3-dihydro-1H-phenalen-1-yl)-piperidine4-carbonitrile without isolation of the intermediate amide.

EXAMPLE 68

(S)-8-(Acenaphthen-1-yl)-1-phenyl-1,3,8-triaza-spiro[4.5]decan-4-one hydrochloride (1:1)

The title compound, light brown solid, m.p. 253° C. and MS: m/e=384.3 (M+H$^+$) was prepared in accordance with the general methods of example aa and 44 from (S)-4-phenylamino-1-(acenaphthen-1-yl)-piperidine-4-carbonitrile without; isolation of the intermediate amide.

EXAMPLE 69
(R)-8-(Acenaphthen-1-yl)-1-phenyl-1,3,8-triaza-spiro[4.5]decan-4-one hydrochloride (1:1)

The title compound, white solid, m.p. 270° C. and MS: m/e=384.3 (M+H$^+$) was prepared in accordance with the general methods of examples aa and 44 from (R)-4-phenylamino-1-(acenaphthen-1-yl)-piperidine4-carbonitrile without isolation of the intermediate amide.

EXAMPLE 70
8-(2,3,3a,4,5,6-Hexadydro-1H-phenalen-1-yl)-1-phenyl-1,3,8-triaza-spiro[4.5]decan-4-one hydrochloride (1:1)

The title compound, white solid, m.p. 246° C. and MS: m/e=402.4 (M+H$^+$) was prepared in accordance with the general method of example 11 from 2,3,3a,4,5,6-hexahydro-phenalen-1-one oxime and 1-phenyl-1,3,8-triazaspiro[4.5]decan-4-one.

EXAMPLE 71
8-(Fluoren-9-yl)-1-phenyl-1,3,8-triaza-spiro[4.5]decan-4-one hydrochloride (1:1)

The title compound, white solid, m.p. 285° C. and MS: m/e=396.1 (M+H$^+$) was prepared in accordance with the general methods of examples aa and 44 from 4-phenylamino-1-(fluoren-9-yl)-piperidine-4-carbonitrile without isolation of the intermediate amide.

EXAMPLE 72
(RS)-8-(5-Methyl-1,2,3,4-tetrahydro-naphthalen-1-yl)-1-phenyl-1,3,8-triaza-spiro[4.5]decan-4-one hydrochloride (1:1)

The title compound, m.p.>250° C. and MS: m/e=376.3 (M+H$^+$) was prepared in accordance with the general method of example 11 from 5-methyl-3,4-dihydro-1(2H)-naphthalenone oxime and 1-phenyl-1,3,8-triazaspiro[4.5]decan-4-one.

EXAMPLE 73
(RS)-8-(Acenaphthen-1-yl)-1-(3-chloro-phenyl)-1,3,8-triaza-spiro[4.5]decan-4-one hydrochloride (1:1)

The title compound, white solid, m.p. 272° C. and MS: m/e=418.2 (M+H$^+$) was prepared in accordance with the general methods of examples aa and 44 from (RS)-1-(acenaphthen-1-yl)-4-(3-chloro-phenylamino)-piperidine-4-carbonitrile without isolation of the intermediate amide.

EXAMPLE 74
(RS)-8-(Acenaphthen-1-yl)-1-(m-tolyl)-1,3,8-triaza-spiro[4.5]decan-4-one hydrochloride (1:1)

The title compound, white solid, m.p. 268° C. and MS: m/e=398.3 (M+H$^+$) was prepared in accordance with the general methods of examples aa and 44 from (RS)-1-(acenaphthen-1-yl)-4-(m-tolylamino)-piperidine-4-carbonitrile without isolation of the intermediate amide.

EXAMPLE 75
(RS)-8-(Acenaphthen-1-yl)-1-(p-tolyl)-1,3,8-triaza-spiro[4.5]decan-4-one hydrochloride (1:1)

The title compound, white solid, m.p. 266° C. and MS: m/e=398.3 (M+H$^+$) was prepared in accordance with the general methods of examples aa and 44 from (RS)-1-(acenaphthen-1-yl)-4-(p-tolylamino)-piperidine-4-carbonitrile without isolation of the intermediate amide.

EXAMPLE 76
(RS)-8-(Acenaphthen-1-yl)-1-(3-methoxy-phenyl)-1,3,8-triaza-spiro[4.5]decan-4-one hydrochloride (1:1)

The title compound, white solid, m.p. 274° C. and MS: m/e=414.2 (M+H$^+$) was prepared in accordance with the general methods of examples aa and 44 from (RS)-1-(acenaphthen-1-yl)-4-(3-methoxy-phenylamino)-piperidine-4-carbonitrile without isolation of the intermediate amide.

EXAMPLE 77
(RS)-8-(Acenaphthen-1-yl)-1-(4-methoxy-phenyl)-1,3,8-triaza-spiro[4.5]decan-4-one hydrochloride (1:1)

The title compound, white solid, m.p. 262° C. and MS: m/e=414.2 (M+H$^+$) was prepared in accordance with the general methods of examples aa and 44 from (RS)-1-(acenaphthen-1-yl)-4-(4-methoxy-phenylamino)-piperidine-4-carbonitrile without isolation of the intermediate amide.

Synthesis of Intermediates

EXAMPLE aa
(S)-1-Indan-1-yl-4-phenylamino-piperidine-4-carboxylic acid amide (S)-1-Indan-1-yl-4-phenylamino-piperidine-4-carbonitrile (27 mmol) was added dropwise at room temperature to a mixture of acetic anhydride and formic acid (40 ml each). The mixture was stirred for 16 h at room temperature. Sodium hydroxide solution was added (pH=7) and the mixture extracted with ethyl acetate. Organic phases were pooled, dried with sodium sulfate and concentrated. Chromatography on silica gel (ethyl acetate) yielded the formulated amine which was dissolved in t-butanol (60 ml). Ammonia (28%, 10 ml), water (10 ml) and hydrogen peroxide solution (33% in water, 5 ml) were added. The mixture was stirred for 2.5 h at room temperature (RT, about 22° C.), quenched with cold water (50 ml) and extracted with methylene chloride. Organic phases were pooled, dried with sodium sulfate and concentrated. Chromatography on silica gel (methylene chloride/methanol, 98:2) yielded the desired product as a solid. 1.0 g (11%) of (S)-1-indan-1-yl-4-phenylamino-piperidine-4-carboxylic acid amide, m.p. 194–195° C. and MS: m/e=336.2 (M+H$^+$).

EXAMPLE ab
(S)-1-Indan-1-yl-4-phenylamino-piperidine-4-carbonitrile (S)-1-Indan-1-yl-piperidine-4-one (31 mmol) was dissolved in acetic acid (28 ml). Aniline (33 mmol) and trimethylsilylcyanide (31 mmol) were added and the mixture was stirred for 45 min. at room temperature. The reaction mixture was poured into cold ammonia solution (water/28% ammonia, 50 ml/30 ml). The solution was adjusted to pH 10 and extracted with methylene chloride. Organic phases were pooled, dried with sodium sulfate and concentrated. Crystallization from diethylether yielded the desired product as a solid. 8.1 g (80%) of (S)-1-indan-1-yl-4-phenylamino-piperidine-4-carbonitrile, m.p. 157–160° C. and MS: m/e=318.3 (M+H$^+$).

EXAMPLE ac
(S)-1-Indan-1-yl-piperidine-4-one (S)-1-Aminoindane (37 mmol) was dissolved in ethanol (65 ml). Potassium carbonate (3.7 mmol) and 1-ethyl-1-methyl-4-oxo-piperidinium iodide (56 mmol) dissolved in water (30 ml) were added and the mixture was refluxed for 30 mil. Water was added, ethanol was removed in vacuo and the residue was extracted with ethyl acetate. Organic phases were pooled, dried with sodium sulfate and concentrated.

Chromatography on silica gel (ethyl acetate) yielded the desired product as an oil. 7.1 g (90%) of (S)-1-indan-1-yl-piperidine-4-one, MS: m/e=216.4 (M+H⁺).

EXAMPLE ad
(R)-1-Indan-1-4l-4phenylamino-piperidine-4-carboxylic acid amide

The title compound, m.p. 193-195° C. and MS: m/e=336.2 (M+H⁺) was prepared. in accordance with the general method of example aa from (R)-1-Indan-1-yl-4-phenylamino-piperidine-4-carbonitrile.

EXAMPLE af
(R)-1-Indan-1-yl-4-phenylamino-piperidine-4-carbonitrile

The title compound, m.p. 158–1590C and MS: m/e=318.3 (M+H⁺) was prepared in accordance with the general method of example ab from (R)-1-indan-1-yl-piperidine-4-one, aniline and trimethylsilylcyanide.

EXAMPLE ag
(R)-1-Indan-1-yl-piperidine-4-one

The title compound, MS: m/e=216.4 (M+H⁺) was prepared in accordance with the general method of example ac from (R)-1-aminoindane and 1-ethyl-1-methyl-4-oxo-piperidinium iodide.

EXAMPLE ah
(R)-4-Phenylamino-1-(1,2,3,4-tetrahydro-naphtalen-1-yl)-piperidine-carboxylic acid amide The title compound, m.p. 182–184 0C and MS: m/e=350.3 (M+H⁺) was prepared in accordance with the general method of example aa from (R)4phenylamino-1-(1,2,3,4-tetrahydro-naphtalen-1-yl)-piperidine-carbonitrile.

EXAMPLE ai
(R)-4-Phenylamino-1-(1,2,3,4-tetrahydro-naphtalen-1-yl)-piperidine-4-carbonitrile (R)-1,2,3,4-Tetrahydro-1-naphthylamine (16 mmol) was dissolved in ethanol (30 ml). Potassium carbonate (9.3 mmol) and 1-ethyl-1-methyl-4-oxo-piperidinium iodide (23 mmol) dissolved in water (30 ml) were added and the mixture was refluxed for 1 h. Water was added, ethanol was removed in vacuo and the residue was extracted with ethyl acetate. Organic phases were pooled, dried with sodium sulfate and concentrated. Chromatography on silica gel (ethyl acetate) yielded (R)-1-(1,2,3,4-tetrahydro-naphtalen-1-yl)-piperidine-4-one which was dissolved in acetic acid (11 ml). Aniline (14 mmol) and trimethylsilylcyanide (13 mmol) were added and the mixture was stirred for 1.5 h at room temperature. The reaction mixture was poured into cold ammonia solution (water/28% ammonia, 70 ml/30 ml). The solution was adjusted to pH 10 and extracted with methylene chloride. Organic phases were pooled, dried with sodium sulfate and concentrated. Crystallization from diethylether yielded the desired product as a solid. 8.1 g (80%) of (R)4-phenylamino-1-(1,2,3,4-tetrahydro-naphtalen-1-yl)-piperidine-4-carbonitrile, m.p. 152–153° C. and MIS: m/e=332.3 (M+H⁺).

EXAMPLE aj
(S)-4-Phenylamino-1-(1,2,3,4-tetrahydro-naphtalen-1-yl)-piperidine-4-carboxylic acid amide The title compound, m.p. 186–187° C. and MS: m/e=350.3 (M+H⁺) was prepared in accordance with the general method of example aa from (S)-4-phenylamino-1-(1,2,3,4-tetrahydro-naphtalen-1-yl)-piperidine-4-carbonitrile.

EXAMPLE ak
(S)-4-Phenylamino-1-(1,2,3,4-tetrahydro-naphtalen-1-yl)-piperidine-4 carbonitrile The title compound, m.p. 152–153° C. and MS: m/e=332.3 (M+H⁺) was prepared in accordance with the general method of example ai from (S)-1,2,3,4-tetrahydro-1-naphthylamine.

EXAMPLE al
(RS)-2,3-Dihydro-1H-phenalen-1-yl-amine

To a stirred mixture of 2,3-dihydro-phenalen-1-one (1.32 g, 7.24 mmol), hydroxylamine hydrochloride (0.85 g, 12.2 mmol) and water (6 ml) was added dropwise at 75° C. MeOH (7.5 ml) and afterwards a solution of sodium acetate (2.58 g, 19.0 mmol) in water (4 ml). Stirring was continued over a period of 1.5, h, water (20 ml) was added and after cooling (ice bath) the solid was collected by filtration. After drying in vacuo the crude product was dissolved in 3.5 N NH₃/MeOH (100 ml) and hydrogenated over Raney-Nickel (0.5 g, washed with MeOH) at RT for 17h. The catalyst was filtered off, the solution evaporated in vacuo and the residue purified by column chromatography on silica gel (dichloromethane/MeOH 9:1) to yield (RS)-2,3-dihydro-1H-phenalen-1-yl-amine (0.95 g) as a brown oil.

EXAMPLE am
(RS)-1-(2,3-Dihydro-1H-phenalen-1-yl)-piperidine-4-one

The title compound, brown oil, was prepared in accordance with the general method of example ac from (RS)-2,3-dihydro-1H-phenalen-1-yl-amine and 1-ethyl-1-methyl-4-oxo-piperidinium iodide.

EXAMPLE an
(RS)-4-Phenylamino-1-(2,3-dihydro-1H-phenalen-1-yl)-piperidine-4-carbonitrile The title compound, pale brown oil, was prepared in accordance with the general method of example ab from (RS)-1-(2,3-dihydro-1H-phenalen-1-yl)-piperidine-4-one.

EXAMPLE ao
(R)-Acenaphthen-1-yl-amine

To a cooled (0° C.) and stirred solution of (S)-acenaphthenol (1.74 g, 10.2 mmol) and diphenyl-phosphorylazide in toluene (17.5 ml) was added DBU (1,8-diazabicyclo[5.4.0]undec-7-ene) (1.86 ml, 12.3 mmol) and stirring was continued at RT over a period of 20 h. The reaction mixture was extracted with toluene (2×50 ml), the combined organic phases washed with water, dried (MgSO₄) and evaporated in vacuo. The crude product was dissolved in EtOH (120 ml) and hydrogenated at RT over PtO₂ (0.24 g). The catalyst was filtered off, the solution evaporated in vacuo and the residue purified by column chromatography on silica gel (dichloromethane/MeOH 9:1) to yield (R)-acenaphthen-1-yl-amine (1.56 g) as a pink oil. MS: m/e=169 (M⁺).

EXAMPLE ap
(S)-Acenaphthen-1-yl-amine

The title compound, pale yellow oil, MS: m/e=169 (M⁺) was prepared in accordance with the general method of example ao from (R)-acenaphthenol.

EXAMPLE aq
(R)-1-(Acenaphthen-1-yl)-piperidine-4-one

The title compound, red-brown oil, MS: m/e=252.2 (M+H⁺) was prepared in accordance with the general method of example ac from (R)-acenaphthen-1-yl-amine and 1-ethyl-1-methyl-4-oxo-piperidinium iodide.

EXAMPLE ar (S)-1-(Acenaphthen-1-yl)-piperidine-4-one

The title compound, red-brown oil, MS: m/e=252.2 (M+H$^+$) was prepared in accordance with the general method of example ac from (S)-acenaphthen-1-yl-amine and 1-ethyl-1-methyl-4-oxo-piperidinium iodide.

EXAMPLE as (R)-4-Phenylamino-1-(acenaphthen-1-yl)-piperidine-4-carbonitrile

The title compound, pale yellow foam, MS: m/e=354.3 (M+H$^+$) was prepared in accordance with the general method of example ab from (R)-1-(acenaphthen-1-yl)-piperidine-4-one.

EXAMPLE at (S)-4-Phenylamino-1-(acenaphthen-1-yl)-piperidine-4-carbonitrile

The title compound, pale yellow oil, MS: m/e=354.3 (M+H$^+$) was prepared in accordance with the general method of example ab from (S)-1-(acenaphthen-1-yl)-piperidine-4-one.

EXAMPLE au 1-(Fluoren-9-yl)-piperidine-4-one

The title compound, red-brown solid, m.p. 135° C., MS: m/e=263 (M$^+$) was prepared in accordance with the general method of example ac from fluoren-9-yl-amine and 1-ethyl-1-methyl-4-oxo-piperidinium iodide.

EXAMPLE av

4-Phenylamino-1-(fluoren-9-yl)-piperidine-4-carbonitrile

The title compound, white solid, m.p. 165° C., MIS: m/e=366.1 (M+H$^+$) was prepared in accordance with the general method of example ab from 1-(fluoren-9-yl)-piperidine-4-one.

EXAMPLE aw (RS)-1-(Acenaphthen-1-yl)-4-(3-chloro-phenylamino)-piperidine-4-carbonitrile The title compound, pale brown foam, MS: m/e=388.1 (M+H$^+$) was prepared in accordance with the general method of example ab from 3-chloro-aniline and (RS)-1-(acenaphthen-1-yl)-piperidine-4-one.

EXAMPLE ax (RS)-1-(Acenaphthen-1-yl)-4-(m-tolylamino)-piperidine-4-carbonitrile The title compound, pale brown foam, MS: m/e=368.2 (M+H$^+$) was prepared in accordance with the general method of example ab from m-toluidine and (RS)-1-(acenaphthen-1-yl)-piperidine-4-one.

EXAMPLE ay (RS)-1-(Acenaphthen-1-yl)-4-(3-methoxy-phenylamino)-piperidine-4-carbonitrile The title compound, pale brown foam, MS: m/e=384.2 (M+H$^+$) was prepared in accordance with the general method of example ab from 3-methoxy-aniline and (RS)-1-(acenaphthen-1-yl)-piperidine-4-one.

EXAMPLE az (RS)-1-(Acenaphthen-1-yl)-4-(4-methoxy-phenylamino)-piperidine-4-carbonitrile The title compound, pale brown foam, MS: m/e=384.2 (M+H$^+$) was prepared in accordance with the general method of example ab from 3-methoxy-aniline and (RS)-1-(acenaphthen-1-yl)-piperidine-4-one.

EXAMPLE ba (RS)-1-(Acenaphthen-1-yl)-4-(p-tolylamino)-piperidine-4-carbonitrile The title compound, pale brown foam, MS: m/e=368.2 (M+H$^+$) was prepared in accordance with the general method of example ab from p-toluidine and (RS)-1-(acenaphthen-1-yl)-piperidine-4-one.

EXAMPLE A

Tablets of the following composition are made in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are made in the usual manner:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are made in the usual manner:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. Compounds of the formula

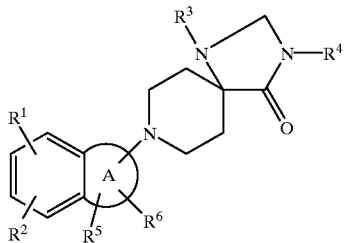

wherein
- $R^1$ and $R^2$ are each independently hydrogen, lower alkyl, lower alkoxy or halogen;
- $R^3$ is phenyl, which is unsubstituted or substituted by lower alkyl, $CF_3$, lower alkoxy or halogen;
- $R^4$ is hydrogen, lower alkyl, lower alkenyl, —C(O)-lower alkyl, —(O)-phenyl, lower alkyl-C(O)-phenyl, lower alkylene-C(O)O-lower alkyl, lower alkantriyl-di-C(O)O-lower alkyl, hydroxy-lower alkyl, lower alkyl-O-lower alkyl, lower alkyl-CH(CH)CF$_3$, phenyl or benzyl,
- $R^5$ and $R^6$ are each independently hydrogen, phenyl, lower alkyl or di-lower alkyl or $R^5$ and $R^6$ together with the carbon atoms to which they are bound form a phenyl ring, or
- $R^5$ and one of $R^1$ or $R^2$ together with the carbon atoms to which they are bound form a saturated or unsaturated 6 membered ring, A is a 4–7 membered non-heterocyclic saturated ring, their racemates and the enantiomers thereof, and the pharmaceutically acceptable acid addition salts thereof.

2. The compound of claim 1, wherein A is a 5 to 7 membered non-heterocyclic saturated ring.

3. The compound of claim 2, wherein A is a 5membered non-heterocyclic saturated ring.

4. The compound of claim 3, wherein $R^4$ is hydrogen, lower alkyl, lower alkenyl, —C(O)-lower alkyl, —C(O)-phenyl, lower alkyl-C(O)-phenyl, lower alkylene-C(O)O-lower alkyl, hydroxy-lower alkyl, lower alkyl-O-lower alkyl, lower alkyl-CH(OH)CF$_3$, or benzyl.

5. The compound of claim 4, wherein $R^4$ is hydrogen or lower alkyl.

6. The compound of claim 5, wherein $R^4$ is hydrogen.

7. The compound of claim 6, wherein $R^3$ is phenyl which is unsubstituted or substituted with lower alkyl, lower alkoxy or halogen.

8. The compound of claim 7, wherein $R^3$ is phenyl which is unsubstituted.

9. The compound of claim 8, wherein $R^1$ is hydrogen and $R^2$ is hydrogen.

10. The compound of claim 9, (RS)-8-Indan-1-yl-1-phenyl-1,3,8-triaza-spiro[4.5]decan-4-one.

11. The compound of claim 9, 8-Indan-2-yl-1-phenyl-1,3,8-triaza-spiro[4.5]decan-4-one.

12. The compound of claim 9, (R)-8-Indan-1-yl-1-phenyl-1,3,8-triaza-spiro[4.5]decan-4-one.

13. The compound of claim 9, (S)-8-Indan-1-yl-1-phenyl-1,3,8-triaza-spiro[4.5]decan-4-one.

14. The compound of claim 5, wherein $R^4$ is lower alkyl.

15. The compound of claim 14, 8-Indan-2-yl-3-methyl-1-phenyl-1,3,8-triaza-spiro[4.5]decan-4-one.

16. The compound of claim 14, (RS)-8-Indan-1-yl-3-methyl-1-phenyl-1,3,8-triaza--spiro[4.5]decan-4-one.

17. The compound of claim 8, wherein $R^1$ is hydrogen and $R^2$ is lower alkyl.

18. The compound of claim 17, (RS)-8-(5-iso-Propyl-indan-1-yl)-1-phenyl-1,3,8-triaza--spiro[4.5]decan-4-one.

19. The compound of claim 17, (RS)-8-(5-Methyl-indan-1-yl)-1-phenyl-1,3,8-triaza-spiro[4.5]decan-4-one.

20. The compound of claim 17, (RS)-1-Phenyl-8-(3,3,6-trimethyl-indan-1-yl)-1,3,8-triaza--spiro[4.5]decan-4-one.

21. The compound of claim 8, wherein $R^1$ is hydrogen and $R^2$ is lower alkoxy.

22. The compound of claim 21, (RS)-8-(4-Methoxy-indan-1-yl)-1-phenyl-1,3,8-triaza-spiro[4.5]decan-4-one.

23. The compound of claim 21, (RS)-8-(5-Methoxy-indan-1-yl)-1-phenyl-1,3,8-triaza-spiro[4.5]decan-4-one.

24. The compound of claim 21, (RS)-8-(6-Methoxy-indan-1-yl)-1-phenyl-1,3,8-triaza-spiro[4.5]decan-4-one.

25. The compound of claim 8, wherein $R^1$ is hydrogen and $R^2$ is halogen.

26. The compound of claim 25, (RS)-8-(5-Chloro-indan-1-yl)-1-phenyl-1,3,8-triaza--spiro[4.5]decan-4-one.

27. The compound of claim 25, (RS)-8-(4Chloro-indan-1-yl)-1-phenyl-1,3,8-triaza--spiro[4.5]decan-4-one.

28. The compound of claim 8, wherein $R^5$ is lower alkyl or phenyl.

29. The compound of claim 27, wherein $R^5$ is lower alkyl.

30. The compound of claim 29, 8-(3-methyl-indan-1-yl)-1-phenyl-1,3,8-triaza-spiro[4.5]decan-4-one, which is a mixture of (1RS,3RS) and (1RS,3SR) racemates.

31. The compound of claim 28, wherein $R^5$ is phenyl.

32. The compound of claim 30, 1-phenyl-8-(3-phenyl-indan-1-yl)-1,3,8-triaza-spiro[4.5]decan-4-one, which is a mixture of (1RS,3RS) and (1RS,3SR) racemates.

33. The compound of claim 7, wherein $R^2$ and $R^5$ together with the carbon. atom to which they are attached form an unsaturated ring.

34. The compound of claim 33, wherein $R^3$ is phenyl which is unsubstituted.

35. The compound of claim 34, (RS)-8-(Acenaphthen-1-yl)-1-phenyl-1,3,8-triaza-spiro[4.5]decan-4-one.

36. The compound of claim 33, (S)-8-(Acenaphthen-1-yl)-1-phenyl-1,3,8-triaza-spiro[4.5]decan-4-one.

37. The compound of claim 35, (R)-8-(Acenaphthen-1-yl)-1-phenyl-1,3,8-triaza-spiro[4.5]decan-4-one.

38. The compound of claim 33, wherein $R^3$ is phenyl which is substituted with lower alkyl, lower alkoxy, or halogen.

39. The compound of claim 38, wherein $R^3$ is phenyl which is substituted with lower alkyl.

40. The compound of claim 39, (RS)-8-(Acenaphthen-1-yl)-1-(m-tolyl)-1,3,8-triaza-spiro[4.5]decan-4-one.

41. The compound of claim 39, (RS)-8-(Acenaphthen-1-yl)-1-(p-tolyl)-1,3,8-triaza--spiro[4.5]decan-4-one.

42. The compound of claim 38, wherein $R^3$ is phenyl which is substituted with lower alkoxy.

43. The compound of claim 42, (RS)-8-(Acenaphthen-1-yl)-1-(3-methoxy-phenyl)-1,3,8-triaza-spiro[4.5]decan-4-one.

44. The compound of claim 43, (RS)-8-(Acenaphthen-1-yl)-1-(4-methoxy-phenyl)-1,3,8-triaza-spiro[4.5]decan-4-one.

45. The compound of claim 38, wherein $R^3$ is phenyl which is substituted with halogen.

46. The compound of claim 45, (RS)-8-(Acenaphthen-1-yl)-1-(3-chloro-phenyl)-1,3,8-triaza-spiro[4.5]decan-4-one.

47. The compound of claim 14, wherein $R^2$ and $R^5$ together with the carbon atom to which they are attached form an unsaturated ring.

48. The compound of claim 47, (RS)-8-(Acenaphthen-1-yl)-3-methyl-1-phneyl-1,3,8-triaza-spiro[4.5]decan-4-one.

49. The compound of claim 7, wherein $R^2$ and $R^5$ together with the carbon atom to which they are attached form a saturated ring.

50. The compound of claim 49, 8-(1,2,2a,3,4,5-Hexahydro-acenaphthen-1-yl)-1-phenyl-1,3,8-triaza-spiro[4.5]decan-4-one, which is a mixture of diastereomeric racemates.

51. The compound of claim 7, wherein $R^5$ and $R^6$ together with the carbon atoms to which they are attached form a phenyl ring.

52. The compound of claim 51, 8-(Fluoren-9-yl)-1-phenyl-1,3,8-triaza-spiro[4.5]decan-4-one.

53. The compound of claim 2, wherein A is a 6-membered non-heterocyclic saturated ring.

54. The compound of claim 58, wherein $R^3$ is phenyl which is unsubstituted.

55. The compound of claim 54, wherein $R^4$ is hydrogen, lower alkyl, lower alkenyl, —C—(O)-lower alkyl, —C—(O)-phenyl, lower alkyl-C—(O)-phenyl, lower alkylene-C—(O)O-lower alkyl, hydroxy-lower alkyl, lower alkyl-O-lower alkyl, lower alkyl-CH(OH)CF$_3$, or benzyl.

56. The compound of claim 60, wherein $R^4$ is hydrogen.

57. The compound of claim 56, wherein $R^1$ is hydrogen and $R^2$ is hydrogen.

58. The compound of claim 57, 1-phenyl-8-(1,2,3,4-tetrahydro-2-naphthyl)-1,3,8-triaza-spiro[4.5]decan-4-one.

59. The compound of claim 57, 1-phenyl-8-(1,2,3,4-tetrahydro-1-naphthyl)-1,3,8-triaza-spiro[4.5]decan-4-one.

60. The compound of claim 57, (R)-1-phenyl-8-(1,2,3,4-tetrahydro-naphthalen-1-yl)-1,3,8-triaza-spiro[4.5]decan-4-one.

61. The compound of claim 57, (S)-1-phenyl-8-(1,2,3,4-tetrahydro-naphthalen-1-yl)-1,3,8-triaza-spiro[4.5]decan-4-one.

62. The compound of claim 57, wherein $R^5$ is phenyl and $R^6$ is hydrogen.

63. The compound of claim 62, 8-(3-Phenyl-1,2,3,4-tetrahydro-naphthalen-1-yl)-1-phenyl-1,3,8-triaza-spiro[4.5]decan-4-one, which is a mixture of diastereomeric racemates.

64. The compound of claim 57, wherein $R^2$ and $R^5$ together with the carbon atom to which they are attached form an unsaturated ring.

65. The compound of claim 64, (RS)-8-(2,3-Dihydro-1H-phenalen-1-yl)-1-phenyl-1,3,8-triaza-spiro[4.5]decan-4-one.

66. The compound of claim 57, wherein $R^2$ and $R^5$ together with the carbon atom to which they are attached form a saturated ring.

67. The compound of claim 66, (RS)-8-(2,3,3a,4,5,6-Hexahydro-1H-phenalen-1-yl)-1-phenyl-1,3,8-triaza-spiro[4.5]decan-4-one.

68. The compound of claim 55, wherein $R^4$ is lower alkyl.

69. The compound of claim 68, (RS)-3-methyl-1-phenyl-8-(1,2,3,4-tetrahydro-naphthalen-1-yl)-1,3,8-triaza-spiro[4.5]decan-4-one.

70. The compound of claim 55, wherein $R^4$ is lower alkyl-CH(OH)CF$_3$.

71. The compound of claim 70, 1-phenyl-8-[1,2,3,4-tetrahydro-naphthalen-2-yl]-3-[(S)-4,4,4trifluoro-3-hydroxy-butyl]-1,3,8-triaza-spiro[4.5]decan-4-one, which is a mixture of 8-[(R)- and (S)-] racemates.

72. The compound of claim 70, 1-phenyl-8-[1,2,3,4-tetrahydro-naphthalen-2-yl]-3-[(R)-4,4,4-trifluoro-3-hydro-butyl]-1,3,8-triaza-spiro[4.5]decan-4-one, which is a mixture of 8-[(R)- and (S)-] racemates.

73. The compound of claim 56, wherein $R^1$ is hydrogen and $R^2$ is lower alkyl.

74. The compound of claim 73, (RS)-8-(5-methyl-1,2,3,4tetrahydro-naphthalen-1-yl)-1-phenyl-1,3,8-triaza-spiro[4.5]decan-4-one.

75. The compound of claim 56, wherein $R^1$ is hydrogen and $R^2$ is lower alkoxy.

76. The compound of claim 75, (RS)-8-(6-methoxy-1,2,3,4-tetrahydro-naphthalen-1-yl)-1-phenyl-1,3,8-triaza-spiro[4.5]decan-4-one.

77. The compound of claim 75, (RS)-8-(5-methoxy-1,2,3,4-tetrahydro-naphthalen-1-yl)-1-phenyl-1,3,8-triaza-spiro[4.5]decan-4-one.

78. The compound of claim 75, (RS)-8-(7-methoxy-1,2,3,4-tetrahydro-naphthalen-1-yl)-1-phenyl-1,3,8-triaza-spiro[4.5]decan-4-one.

79. The compound of claim 56, wherein $R^1$ is hydrogen and $R^2$ is halogen.

80. The compound of claim 79, 8-(6-chloro-1,2,3,4-tetrahydro-2-naphthyl)-1-phenyl-1,3,8-triaza-spiro[4.5]decan-4-one.

81. The compound of claim 79, 8-(8-chloro-1,2,3,4-tetrahydro-2-naphthyl)-1-phenyl-1,3,8-triaza-spiro[4.5]decan-4-one.

82. The compound of claim 79, 8-(7-chloro-1,2,3,4-tetrahydro-2-naphthyl)-1-phenyl-1,3,8-triaza--spiro[4.5]decan-4-one.

83. The compound of claim 79, 8-(5-chloro-1,2,3,4-tetrahydro-2-naphthyl)-1-phenyl-1,3,8-triaza-spiro[4.5]decan-4-one.

84. The compound of claim 79, (RS)-8-(5-chloro-1,2,3,4-tetrahydro-2-naphthalen-1-yl)-1-phenyl-1,3,8-triaza-spiro[4.5]decan-4-one.

85. The compound of claim 79, (RS)-8-(7-fluoro-1,2,3,4-tetrahydro-2-naphthalen-1-yl)-1-phenyl-1,3,8-triaza-spiro[4.5]decan-4-one.

86. The compound of claim 79, (RS)-8-(7-chloro-1,2,3,4-tetrahydro-2-naphthalen-1-yl)-1-phenyl-1,3,8-triaza-spiro[4.5]decan-4-one.

87. The compound of claim 79, (RS)-8-(6-chloro-1,2,3,4tetrahydro-2-naphthalen-1-yl)-1-phenyl-1,3,8-triaza-spiro[4.5]decan-4-one.

88. The compound of claim 79, (RS)-8-(8-bromo-1,2,3,4-tetrahydro-2-naphthalen-1-yl)-1-phenyl-1,3,8-triaza-spiro[4.5]decan-4-one.

89. The compound of claim 55, wherein $R^4$ is lower alkyl.

90. The compound of claim 89, wherein $R^1$ is hydrogen and $R^2$ is halogen.

91. The compound of claim 90, 8-(6-chloro-1,2,3,4tetrahydro-2-naphthyl)-3-methyl-1-phenyl-1,3,8-triaza-spiro[4.5]decan-4-one.

92. The compound of claim 90, 8-(8-chloro-1,2,3,4-tetrahydro-2-naphthyl)-3-methyl-1-phenyl-1,3,8-triaza--spiro[4.5]decan-4-one.

93. The compound of claim 55, wherein $R^4$ is lower alkyl-C—(O)-phenyl.

94. The compound of claim 93, wherein $R^1$ is hydrogen and halogen.

95. The compound of claim 94, (RS)-8-(8-chloro-1,2,3,4-tetrahydro-naphthalen-2-yl)-3-(2-oxo-2-phenyl-ethyl)-1-phenyl-1,3,8-triaza-spiro[4.5]decan-4-one.

96. The compound of claim 56, wherein $R^1$ is halogen and $R^2$ is halogen.

97. The compound of claim 96, (RS)-8-(7-Chloro-5-fluoro-1,2,3,4-tetrahydro-naphthalen-1-yl)-1-phenyl-1,3,8-triaza-spiro[4.5]decan-4-one.

98. The compound of claim 96, 8-(5,8-Dichloro-1,2,3,4-tetrahydro-naphthyl-2)-1-phenyl-1,3,8-triaza-spiro[4.5]decan-4-one.

99. The compound of claim 96, (−)-8-(5,8-Dichloro-1,2,3,4-tetrahydro-naphthyl-2)-1-phenyl-1,3,8-triaza-spiro[4.5]decan-4-one.

100. The compound of claim 96, (+)-8-(5,8-Dichloro-1,2,3,4-tetrahydro-naphthyl-2)-1-phenyl-1,3,8-triaza-spiro[4.5]decan-4-one.

101. The compound of claim 56, wherein $R^1$ is lower alkyl and $R^2$ is lower alkyl.

102. The compound of claim 101, 8-(5,7-Dimethyl-1,2,3,4-tetrahydro-naphthyl-2)-1-phenyl-1,3,8-triaza-spiro[4.5]decan-4-one.

103. The compound of claim 101, (RS)-8-(5,8-Dimethyl-1,2,3,4tetrahydro-naphthalen-2-yl)-1-phenyl-1,3,8-triaza-spiro[4.5]decan-4-one.

104. The compound of claim 55, wherein $R^4$ is lower alkyl.

105. The compound of claim 104, wherein $R^1$ is halogen and $R^2$ is halogen.

106. The compound of claim 105, 8-(5,8-Dichloro-1,2,3,4-tetrahydro-naphthyl-2)-3-methyl-1-phenyl-1,3,8-triaza-spiro[4.5]decan-4-one.

107. The compound of claim 105, 8-(5,8-Dichloro-1,2,3,4-tetrahydro-naphthyl-2)-3-ethyl-1-phenyl-1,3,8-triaza-spiro[4.5]decan-4-one.

108. The compound of claim 55, wherein $R^4$ is lower alkenyl.

109. The compound of claim 108, wherein $R^1$ is halogen and $R^2$ is halogen.

110. The compound of claim 109, 3-Allyl-8-(5,8-dichloro-1,2,3,4tetrahydro-naphthyl-2)-1-phneyl-1,3,8-triaza-spiro[4.5]decan-4-one.

111. The compound of claim 55, wherein $R^4$ is benzyl.

112. The compound of claim 111, wherein $R^1$ is halogen and $R^2$ is halogen.

113. The compound of claim 112, 3-Benzyl-8-(5,8-dichloro-1,2,3,4-tetrahydro-naphthyl-2)-1-phenyl-1,3,8-triaza-spiro[4.5]decan-4-one.

114. The compound of claim 55, wherein $R^4$ is —C(O)-lower alkyl.

115. The compound of claim 114, wherein $R^1$ is halogen and $R^2$ is halogen.

116. The compound of claim 115, 3-Acetyl-8-(5,8-dichloro-1,2,3,4-tetrahydro-naphthyl-2)-1-phenyl-1,3,8-triaza-spiro[4.5]decan-4-one.

117. The compound of claim 55, wherein $R^4$ is —C(O)-phenyl.

118. The compound of claim 117, wherein $R^1$ is halogen and $R^2$ is halogen.

119. The compound of claim 118, (RS)-3-Benzoyl-8-(5,8-dichloro-1,2,3,4-tetrahydro-naphthalen-2-yl)-1-phenyl-1,3,8-triaza-spiro[4.5]decan-4-one.

120. The compound of claim 55, wherein $R^4$ is lower alkylene-C(O)O-lower alkyl.

121. The compound of claim 120, wherein $R^1$ is halogen and $R^2$ is halogen.

122. The compound of claim 121, [8-(5,8-Dichloro-1,2,3,4-tetrahydro-naphthyl-2)-4-oxo-1-phenyl-1,3,8-triaza-spiro[4.5]dec-3-yl]-aceticacid methylester.

123. The compound of claim 55, wherein $R^4$ is lower alkantriyl-di-C(O)O-lower alkyl.

124. The compound of claim 123, wherein $R^1$ is halogen and $R^2$ is halogen.

125. The compound of claim 124, (RS)-2-[8-(5,8-Dichloro-1,2,3,4-tetrahydro-naphthalen-2-yl)-4-oxo-1-phenyl-1,3,8-triaza-spiro[4.5]dec-3-yl]-maloniacid dimethyl ester.

126. The compound of claim 55, wherein $R^4$ is hydroxy-lower alkyl.

127. The compound of claim 126, wherein $R^1$ is hydrogen and $R^2$ is halogen.

128. The compound of claim 127, (RS)-8-(8-Chloro-1,2,3,4-tetrahydro-naphthalen-2-yl)-3-(2-hydroxy-ethyl)-1-phenyl-1,3,8-triaza-spiro[4.5]decan-4-one.

129. The compound of claim 55, wherein $R^4$ is lower alkyl-O-lower alkyl.

130. The compound of claim 129, wherein $R^1$ is hydrogen and $R^2$ is halogen.

131. The compound of claim 130, (RS)-8-(8-Chloro-1,2,3,4tetrahydro-naphthalen-2-yl)-3-methoxymethyl-1-phenyl-1,3,8-triaza-spiro[4.5]decan-4-one.

132. The compound of claim 2, wherein A is a 7-membered non-heterocyclic saturated ring.

133. The compound of claim 133, wherein $R^3$ is phenyl which is unsubstituted.

134. The compound of claim 133, wherein $R^4$ is hydrogen, lower alkyl, lower alkenyl, —C—(O)-lower alkyl, —C—(O)-phenyl, lower alkyl-C—(O)-phenyl, lower alkylene-C—(O)O-lower alkyl, hydroxy-lower alkyl, lower alkyl-O-lower alkyl, lower alkyl-CH(OH)CF$_3$, or benzyl.

135. The compound of claim 134, wherein $R^4$ is hydrogen.

136. The compound of claim 135, wherein $R^1$ is hydrogen and $R^2$ is hydrogen.

137. The compound of claim 136, (RS)-1-Phenyl-8-(6,7,8,9-tetrahydro-5H-benzocyclohepten-5-yl)-1,3,8-triaza-spiro[4.5]decan-4-one.

138. The compound of claim 136, 1-Phenyl-8-(6,7,8,9-tetrahydro-5H-benzocyclohepten-7-yl)-1,3,8-triaza-spiro[4.5]decan-4-one.

139. The compound of claim 135, wherein $R^5$ and $R^6$ together with the carbon atom to which they are attached form a phenyl ring.

140. The compound of claim 139, (RS)-1-Phenyl-8-(6,7,8,9-tetrahydro-5H-benzocyclohepten-5-yl)-1,3,8-triaza-spiro[4.5]decan-4-one.

141. A pharmaceutical composition comprising a compound of formula I

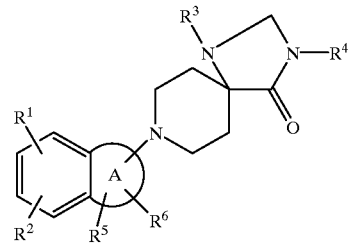

wherein $R^1$ and $R^2$ are each independently hydrogen, lower alkyl, lower alkoxy or halogen;

$R^3$ is phenyl, which is unsubstituted or substituted by lower alkyl, CF$_3$, lower alkoxy or halogen;

$R^4$ is hydrogen, lower alkyl, lower alkenyl, —C(O)-lower alkyl, —C(O)-phenyl, lower alkyl-C(O)-phenyl, lower alkylene-C(O)O-lower alkyl, lower alkantriyl di-C(O)O-lower alkyl, hydroxy-lower alkyl, lower alkyl-O-lower alkyl, lower alkyl-CH(OH)CF$_3$, phenyl or benzyl, $R^5$ and $R^6$ are each independently hydrogen, phenyl, lower alkyl or di-lower alkyl or $R^5$ and $R^6$ together with the carbon atoms to which they are bound form a phenyl ring, or R⁵ and one of R¹ or R² together with the carbon atoms to which they are bound form a saturated or unsaturated 6 membered ring, A is a 4–7 membered non-heterocyclic saturated ring, their racemates and the enantionmers thereof, and the pharmaceutically acceptable acid addition salts thereof and a pharmaceutically acceptable carrier.

142. The composition of claim 141, wherein A is a 6-membered non heterocyclic saturated ring.

143. The composition of claim 142, wherein R³ is phenyl which is unsubstituted.

144. The composition of claim 143, wherein R⁴ is hydrogen, lower alkyl, —C(O)-phenyl, or lower alkylene-C(O)O-lower alkyl.

145. The composition of claim 144, wherein R¹ and R² are each independently hydrogen, lower alkyl, or halogen.

146. The composition of claim 145, wherein the compound of formula I is (−)-8-(5,8-dichloro-1,2,3,4-tetrahydro-naphthyl-2)-1-phenyl-1,3,8-triaza-spiro[4.5]decan-4-one.

147. The composition of claim 145, wherein the compound of formula I is 8-(8-chloro-1,2,3,4-tetrahydro-2-naphthyl)-1-phenyl-1,3,8-triaza-spiro[4.5]decan-4-one.

148. The composition of claim 145, wherein the compound of formula I is 1-phenyl-8-(1,2,3,4-tetrahydro-1-naphthyl)-1,3,8-triaza-spiro[4.5]decan-4-one.

149. The composition of claim 145, wherein the compound of formula I is [8-(5,8-Dichloro-1,2,3,4-tetrahydro-2-naphthyl)-4-oxo-1-phenyl-1,3,8-triaza-spiro[4.5]dec-3-yl]-acetic acid methylester.

150. The composition of claim 145, wherein the compound of formula I is 8-(5,8-Dichloro-1,2,3,4-tetrahydro-2-naphthyl)-3-methyl-1-phenyl-1,3,8-triaza-spiro[4.5]decan-4-one.

151. The composition of claim 145, wherein the compound of formula I is 8-(5,8-Dichloro-1,2,3,4-tetrahydro-2-naphthyl)-3-ethyl-1-phenyl-1,3,8-triaza-spiro[4.5]decan-4-one.

152. The composition of claim 145, wherein the compound of formula I is (RS)-8-(5-Methyl-1,2,3,4-tetrahydro-naphthalen-1-yl)-1-phenyl-1,3,8-triaza-spiro[4.5]decan-4-one.

153. The composition of claim 141, wherein A is a 5 membered non-heterocyclic saturated ring.

154. The composition of claim 153, wherein R³ is phenyl which is unsubstituted.

155. The composition of claim 154, wherein R⁴ is hydrogen.

156. The composition of claim 155, wherein R¹ and R² are each hydrogen.

157. The composition of claim 156, wherein the compound of formula I is 8-Indan-2-yl-1-phenyl-1,3,8-triaza-spiro[4.5]decan-4-one.

158. The composition of claim 154, wherein R² and R⁵ together with the carbon atoms to which they are attached form an unsaturated ring.

159. The composition of claim 158, wherein R⁴ is hydrogen or lower alkyl.

160. The composition of claim 159, wherein the compound of formula I is (RS)-8-(Acenaphthen-1-yl)-1-phenyl-1,3,8-triaza-spiro[4.5]decan-4-one.

161. The composition of claim 159, wherein the compound of formula I is (R)-8-(Acenaphthen-1-yl)-1-phenyl-1,3,8-triaza-spiro[4.5]decan-4-one.

162. The composition of claim 159, wherein the compound of formula I is (RS)-8-(Acenaphthen-1-yl)-3-methyl-1-phenyl-1,3,8-triaza-spiro[4.5]decan-4-one.

163. The composition of claim 144, wherein R² and R⁵ together with the carbon atom to which they are attached form an unsaturated ring.

164. The composition of claim 163, wherein the compound of formula I is (RS)-8-(2,3-Dihydro-1H-phenalen-1-yl)-1-phenyl-1,3,8-triaza-spiro[4.5]decan-4-one.

165. The composition of claim 164, wherein R² and R⁵ together with the carbon atoms to which they are attached form a saturated ring.

166. The composition of claim 165, wherein the compound of formula I is 8-(2,3,3a,4,5,6-Hexahydro-1H-phenalen-1-yl)-1-phenyl-1,3,8-triaza-spiro[4.5]decan-4-one.

167. A method of treating a psychiatric disorder relating to a G-protein coupled receptor which has as a ligand orphanin FQ to ameliorate symptoms of anxiety and stress disorders or depression in a host, comprising administering to the host in need of such treatment a compound of formula I

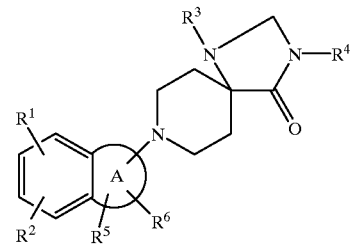

wherein

R¹ and R² are each independently hydrogen, lower allyl, lower alkoxy or halogen;

R³ is phenyl, which is unsubstituted or substituted by lower alkyl, CF₃, lower alkoxy or halogen;

R⁴ is hydrogen, lower alkyl, lower alkenyl, —C(O)-lower alkyl, —C(O)-phenyl, lower alkyl-C(O)-phenyl, lower alkylene-C(O)O-lower alkyl, lower alkantriyl-di-C(O)O-lower alkyl, hydroxy-lower alkyl, lower alkyl-O-lower alkyl, lower alkyl-CH(OH)CF₃, phenyl or benzyl, R⁵ and R⁶ are each independently hydrogen, phenyl, lower alkyl or di-lower alkyl or R⁵ and R⁶ together with the carbon atoms to which they are bound form a phenyl ring, or R⁵ and one of R¹ or R² together with the carbon atoms to which they are bound form a saturated or unsaturated 6 membered ring, A is a 4–7 membered non-heterocyclic saturated ring, their racemates and the enantiomers thereof, the pharmaceutically acceptable acid addition salts thereof, and a pharmaceutically acceptable carrier, in a therapeutically effective amount such that the compound of formula I act as an agonist or an antagonist of the orphanin FQ receptor.

* * * * *

UNITED STATES PATENT AND TRADEMARK OFFICE
CERTIFICATE OF CORRECTION

PATENT NO. : 6,071,925
DATED : June 6, 2000
INVENTOR(S) : Adam et al.

It is certified that error appears in the above-identified patent and that said Letters Patent is hereby corrected as shown below:

Column 25,
Line 22, "-(O)" should read -- - C(O) ---.
Line 25: "alkyl-CH(CH)CF$_3$" should read --- alkyl-CH(OH)CF$_3$ ---.

Column 26,
Line 26: "claim 27," should read --- claim 28, ---.
Line 34: "carbon." should read --- carbon ---.
Line 40: "claim 33," should read --claim 35, ---.

Column 27,
Line 16: "claim 58," should read --- claim 53, ---.
Line 23: "claim 60," should read --- claim 55, ---.

Column 30,
Line 15: "claim 133," should read --- claim 132, ---.

Column 32,
Line 10: "claim 164," should read --- claim 144, ---.

Signed and Sealed this

Seventh Day of August, 2001

*Attest:*

NICHOLAS P. GODICI
*Attesting Officer*   Acting Director of the United States Patent and Trademark Office